US012690786B2

(12) United States Patent
Torres, Jr. et al.

(10) Patent No.: US 12,690,786 B2
(45) Date of Patent: Jul. 28, 2026

(54) CATALYTIC REACTIVE OXYGEN SPECIES SCAVENGER HYDROGEL

(71) Applicant: Senseonics, Incorporated, Germantown, MD (US)

(72) Inventors: Leopoldo Torres, Jr., Germantown, MD (US); Venkata Velvadapu, Germantown, MD (US); Lily Granzow, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 674 days.

(21) Appl. No.: 18/184,523

(22) Filed: Mar. 15, 2023

(65) Prior Publication Data

US 2023/0293064 A1 Sep. 21, 2023

Related U.S. Application Data

(60) Provisional application No. 63/320,439, filed on Mar. 16, 2022.

(51) Int. Cl.
*A61B 5/145* (2006.01)

(52) U.S. Cl.
CPC ...... *A61B 5/14546* (2013.01); *A61B 2503/40* (2013.01); *A61B 2560/028* (2013.01); *A61B 2562/12* (2013.01)

(58) Field of Classification Search
CPC ............ A61B 5/14546; A61B 5/14532; A61B 5/14552; A61B 2503/40; A61B 2560/028; A61B 2562/12
See application file for complete search history.

(56) References Cited

U.S. PATENT DOCUMENTS

| | | | |
|---|---|---|---|
| 5,512,246 | A | 4/1996 | Russell et al. |
| 5,517,313 | A | 5/1996 | Colvin, Jr. |
| 9,414,775 | B2 | 8/2016 | Colvin, Jr. et al. |
| 9,693,714 | B2 | 7/2017 | DeHennis et al. |
| 9,931,068 | B2 | 4/2018 | Huffstetler et al. |
| 2005/0173245 | A1 | 8/2005 | Feldman et al. |
| 2008/0014245 | A1 | 1/2008 | Pacetti et al. |
| 2011/0236989 | A1 | 9/2011 | Suri et al. |
| 2013/0241745 | A1 | 9/2013 | Colvin, Jr. et al. |
| 2014/0349307 | A1 | 11/2014 | Crane et al. |
| 2019/0300724 | A1 | 10/2019 | Chen |

(Continued)

OTHER PUBLICATIONS

Cai, Wenyi et al., "Carboxyl-ebselen-based layer-by-layer films as potential antithrombotic and antimicrobial coatings", Biomaterials, vol. 32, No. 31, Jul. 26, 2011, pp. 7774-7784, XP093351862.

*Primary Examiner* — Tse W Chen
*Assistant Examiner* — Hy Khanh Doan
(74) *Attorney, Agent, or Firm* — Rothwell, Figg, Ernst & Manbeck, P.C.

(57) ABSTRACT

A medical device (e.g., an analyte sensor) that may be implanted within a living animal (e.g., a human) and may be used to measure an analyte (e.g., glucose or oxygen) in a medium (e.g., interstitial fluid, blood, or intraperitoneal fluid) within the animal. The medical device may include a polymer covering at least a portion of a surface of the medical device and a plurality of reactive oxygen species (ROS) scavenger molecules covalently linked to the polymer (e.g., to reduce degradation of an analyte indicator including the polymer).

63 Claims, 8 Drawing Sheets

(56) References Cited

U.S. PATENT DOCUMENTS

| | | | | |
|---|---|---|---|---|
| 2020/0166502 | A1* | 5/2020 | Mai ...................... | G01N 21/648 |
| 2020/0241015 | A1 | 7/2020 | Ouyang et al. | |
| 2020/0268291 | A1 | 8/2020 | Chatterjee et al. | |
| 2023/0068818 | A1 | 3/2023 | Chatterjee et al. | |
| 2023/0293064 | A1 | 9/2023 | Torres, Jr. et al. | |

* cited by examiner

Monomer Spacers

Repeating Units (RUs)

CATALYTIC REACTIVE OXYGEN SPECIES SCAVENGER HYDROGEL

CROSS-REFERENCE TO RELATED APPLICATION

The present application claims the benefit of priority to U.S. Provisional Application Ser. No. 63/320,439, filed on Mar. 16, 2022, which is incorporated herein by reference in its entirety.

BACKGROUND

Field of Invention

The present invention relates generally to continuous reduction of in vivo degradation of medical devices when implanted in a living animal and of analyte sensor moieties when measuring an analyte in a medium of a living animal using a system including a sensor implanted (partially or fully) or inserted into the living animal. Specifically, the present invention relates to an implantable medical device (IMD) (e.g., sensor) that utilizes a catalytic reactive oxygen species scavenger hydrogel for protection of oxidation-sensitive materials.

Discussion of the Background

Partially or fully implanted materials undergo physical, chemical, and biological processes in the body that seek to rid the body of the implanted foreign material. Analyte sensors dependent on fluorescence rely on predictable optical signal over to accurately detect the target biomarker. Reactive oxygen species (ROS) are secreted by immune cells during the lifetime of implanted devices. These ROS are first secreted on the exterior of the device and slowly diffuse into pores and subsequent polymer network. Fluorescent hydrogel properties degrade in the presence of ROS. Degradation processes include oxidation of the fluorescent molecules, compromising the ability to modulate, and change in opacity of the hydrogel network.

A sensor may be implanted (partially or fully) within a living animal (e.g., a human) and used to measure an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in a graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor or other medical device is implanted in the body of a living animal, the animal's immune system may begin to attack the sensor or medical device. For instance, if a sensor or other medical device is implanted in a human, white blood cells may attack the sensor or other medical device as a foreign body, and, in the initial immune system onslaught, neutrophils may be the primary white blood cells attacking the sensor. The defense mechanism of neutrophils includes the release of highly caustic substances known as reactive oxygen species. The reactive oxygen species include, for example, hydrogen peroxide.

Hydrogen peroxide and other reactive species such as reactive oxygen and nitrogen species may degrade the indicator molecules of an analyte indicator. For instance, in indicator molecules having a boronate group, hydrogen peroxide may degrade the indicator molecules by oxidizing the boronate group, thus disabling the ability of the indicator molecule to bind glucose. In addition, such reactive species degrade ester-containing polymers of an analyte indicator, for example, as described by Reid, B. et al. PEG hydrogel degradation and the role of the surrounding tissue environment. J. of Tissue Engr. and Regen. Med. 2015.

Further, a medical device or sensor implanted in a body having a functional analyte indicator has a limited longevity because the functional hydrogel loses biocompatibility, stability, and permeability over time. For example, a fibrous capsule formed from a foreign-body reaction may form, e.g., based on adsorption of a cluster of inflammatory proteins.

There is presently a need in the art for improvements in reducing analyte indicator degradation. There is also a need in the art for continuous analyte sensors having increased longevity.

SUMMARY

The present invention overcomes the disadvantages of prior systems by providing, among other advantages, reduced analyte indicator degradation.

One aspect of the present invention may provide a medical device including a polymer and a plurality of reactive oxygen species (ROS) scavenger molecules. The polymer may be disposed on a surface of the medical device. The plurality of ROS scavenger molecules may be covalently linked to the polymer.

In some aspects, the medical device may be a sensor for measurement of an analyte in a medium within a living animal. In some aspects, the sensor may include a sensor housing and an analyte indicator covering at least a portion of the sensor housing, and the analyte indicator may include the polymer.

In some aspects, each of the plurality of reactive oxygen species (ROS) scavenger molecules may be covalently linked to the polymer via a monomer spacer molecule attached to the polymer. In some aspects, the polymer may have a backbone, and the monomer spacer may be covalently linked to the backbone of the polymer. In some aspects, the polymer may include co-monomers of at least monomers according to Formula Ia: ABC [Formula Ia], where A is an analyte indicator monomer, B is a acrylate, methacrylate, acrylamide, or methacrylamide monomer, C is a polyethylene glycol monomer, A is 0.01 to 10% by weight, B is 1 to 99% by weight, and C is 1 to 99% by weight of Formula Ia.

In some aspects, the polymer may include co-monomers of four monomers according to Formula Ia: ABCD [Formula Ia], where A is an analyte indicator monomer, B is a acrylate, methacrylate, acrylamide, or methacrylamide monomer, C is a polyethylene glycol monomer, D is a compound or a monomer containing boronate or boronic acid moieties, A is 0.01 to 10% by weight, B is 1 to 99% by weight, C is 1 to 99% by weight, and D is 0.01 to 99% by weight of Formula Ia. In some aspects, the compound or the monomer containing boronate or boronic acid moieties may be selected from: a compound of formula II: R—B(OH)$_2$ [Formula II], where R in Formula II is selected from hydrogen, hydroxyl, an alkyl group, an alkoxy group, an amino group, an aryl group, a heteroaryl, a cyclic group, a multicyclic group, and/or $NR_1R_2$; $R_1$ and $R_2$ may be identical or different and each may represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and Formula II may optionally include spacer or linker between R and B, or a phenylboronic acid compound

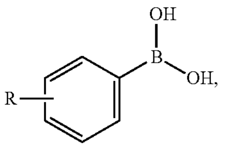

where one or more R in the phenylboronic acid compound is independently selected from hydrogen, hydroxyl, an alkyl group, an alkoxy group, an amino group, an aryl group, a heteroaryl, a cyclic group, a multicyclic group, and/or $NR_1R_2$ where $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, optionally including a spacer or linker between R and B, and/or a boronate compound of Formula III:

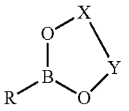

[Formula III], where R in Formula III is independently selected from hydrogen, hydroxyl, an alkyl group, an alkoxy group, an amino group, an aryl group, a heteroaryl, a cyclic group, a multicyclic group, and/or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and wherein X and Y=alkyl, wherein Formula III optionally comprises spacer or linker between R and B, or a combination thereof. In some aspects, the spacer or linker between R and B may be independently selected from a $C_1$-$C_{20}$ linear or branched alkyl or alkoxy. In some aspects, the compound containing boronate or boronic acid moieties may be selected from 2-acrylamidophenylboronic acid, 3-(Acrylamido)phenylboronic acid, 4-vinylboronic acid containing moieties, and (3-methacrylamidophenyl)boronic acid.

In some aspects, the monomer spacer may be covalently linked to the backbone of the polymer comprises a poly (ethylene), poly(ethylene glycol), poly(vinyl alcohol), poly (pyrrolidone), poly(acrylamide), poly(acrylic acid), or poly (amine) group. In some aspects, the poly(ethylene), poly (ethylene glycol), poly(vinyl alcohol), poly(pyrrolidone), poly(acrylamide), poly(acrylic acid), or poly(amine) group may be covalently linked to an acrylate, methacrylate, acrylamide, or methacrylamide group of the polymer.

In some aspects, the monomer spacer covalently linked to the backbone of the polymer may include a flexible spacer having a repeating group selected from:

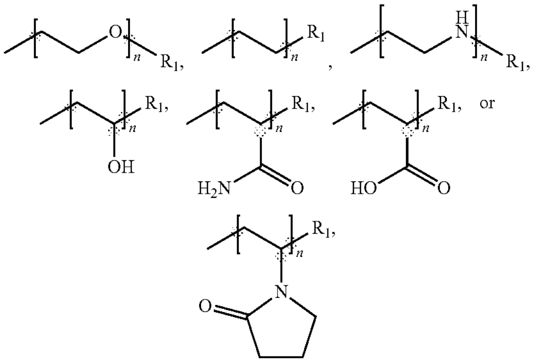

or a combination thereof, and $R_1$ may be a reactive group and wherein n is 1 to 1000. In some aspects, the reactive group may be

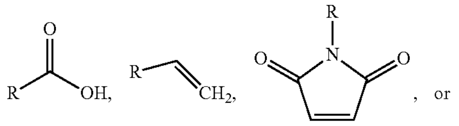

$$R—N=\overset{\oplus}{N}=NH,$$

where R is the repeating group.

In some aspects, the ROS scavenger molecules may include

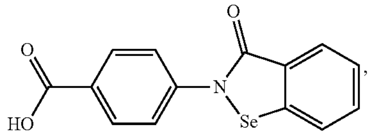

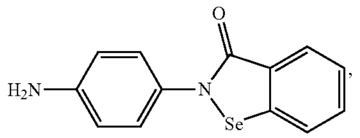

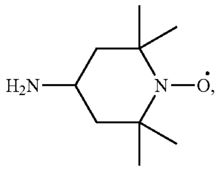

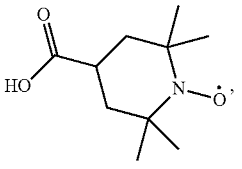

-continued

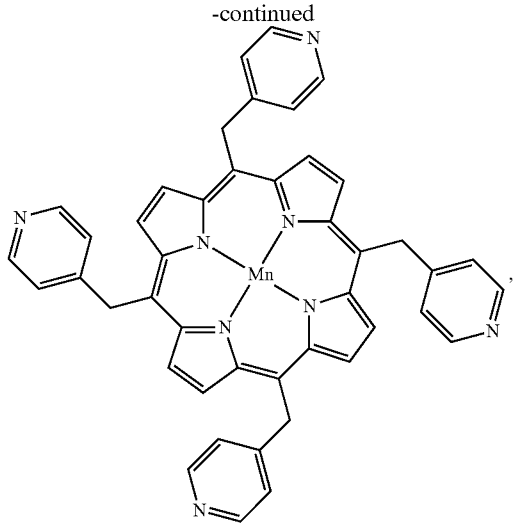

,

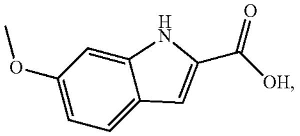

, (6-Methoxyindole-2-carboxylic acid)

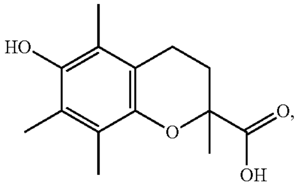

, (6-Hydroxy-2,5,7,8-tetramethylchroman-2-carboxylic acid)

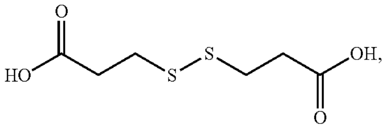

, (3,3′-Dithiodipropionic acid)

or a combination thereof. In some aspects, the ROS scavenger molecules may further include a reactive group attached thereto selected from a primary amine, a thiol, or an alkyne group.

In some aspects, the plurality of ROS scavenger molecules may be covalently linked to the monomer spacer molecule via a coupling bond selected from an amide bond, a carbon-thiol bond, a malamide-thiol bond, or a triazole bond. In some aspects, the coupling bond may be formed between a reactive group RG1 of the monomer spacer molecule and a reactive group RG2 of the ROS scavenger molecules selected from:

| | $RG_1$ | $RG_2$ | Resulting Bond |
|---|---|---|---|
| a) | 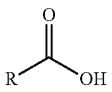 Acid | $H_2N$—R Primary Amine | 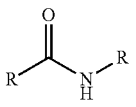 Amide |

-continued

| | $RG_1$ | $RG_2$ | Resulting Bond |
|---|---|---|---|
| b) | 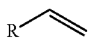 Double Carbon Bond | 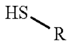 Thiol | 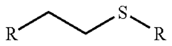 Carbon-Thiol |
| c) | 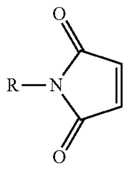 Maleimide | 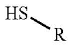 Thiol | 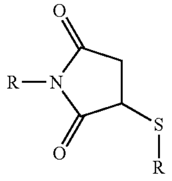 Malamide-Thiol |
| d) | R—N=$\overset{\oplus}{N}$=NH Azide | $\equiv$—R Alkyne | 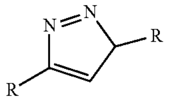 Triazole |

In some aspects, the ROS scavenger molecules may reduce a degradation rate of an analyte indicator including the polymer of the IMD. In some aspects, the ROS scavenger molecules may reduce contact of degradative species with the analyte indicator. In some aspects, the degradative species may be hydrogen peroxide, a reactive oxygen species, a reactive nitrogen species, enzymes, free radical or metal ions.

In some aspects, the analyte indicator may resist biofouling by three- to six-fold longer than an analyte indicator not having said ROS scavenger molecules. In some aspects, the ROS scavenger molecules may not interfere with analyte-binding aspects of the analyte indicator. In some aspects, the ROS scavenger molecules may not interfere with the signaling aspects of the analyte indicator. In some aspects, the ROS scavenger molecules may not leach out of or dissociate from the sensor. In some aspects, the ROS scavenger molecules may reduce chemical degradation and/or oxidation of the sensor. In some aspects, the sensor may include at least one drug eluting polymer matrix that covers a portion of the sensor housing.

Another aspect of the present invention may provide a method of fabricating a medical device. The method may include disposing a polymer on a surface of the medical device. The method may include coupling a plurality of reactive oxygen species (ROS) scavenger molecules covalently to the polymer.

In some aspects, the medical device may be a sensor for measurement of an analyte in a medium within a living animal, disposing the polymer on the surface of the medical device may include applying an analyte indicator to a sensor housing of the sensor such that the applied analyte indicator covers at least a portion of the sensor housing, and the analyte indicator may include the polymer. In some aspects, the polymer may include co-monomers of at least monomers of A) an analyte indicator monomer, B) at least one monomer selected from an acrylate, methacrylate, acrylamide, or methacrylamide having a monomer spacer and a reactive group at an end thereof, and C) a polyethylene glycol monomer. In some aspects, coupling the plurality of ROS scavenger molecules covalently to the polymer may include coupling the plurality of ROS scavenger molecules covalently to the reactive group of the analyte indicator such that each of the plurality of ROS scavenger molecules is covalently linked to the analyte indicator via the monomer spacer. In some aspects, A may be 0.01 to 10% by weight, B may be 1 to 99% by weight, and C may be 1 to 99% by weight of the polymer.

In some aspects, the polymer may include co-monomers of four monomers according to Formula Ia: ABCD [Formula Ia], where A is the analyte indicator monomer, B is the at least one monomer selected from acrylate, methacrylate, acrylamide, or methacrylamide having the monomer spacer and a reactive group at an end thereof, C is the polyethylene glycol monomer, and D is a compound or monomer containing boronate or boronic acid moieties, A is 0.01 to 10% by weight, B is 1 to 99% by weight, C is 1 to 99% by weight, and D is 0.01 to 99% by weight of Formula Ia.

In some aspects, the compound or monomer containing boronate or boronic acid moieties may be selected from: a compound of formula II: R—B$(OH)_2$ [Formula II], where R in Formula II is selected from hydrogen, hydroxyl, an alkyl group, an alkoxy group, an amino group, an aryl group, a heteroaryl, a cyclic group, a multicyclic group, and/or $NR_1R_2$, $R_1$ and $R_2$ may be identical or different and each may represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and Formula II may optionally include spacer or linker between R and B, or a phenylboronic acid compound

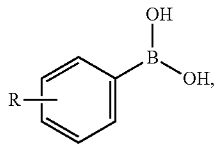

where one or more R in the phenylboronic acid compound is independently selected from hydrogen, hydroxyl, an alkyl group, an alkoxy group, an amino group, an aryl group, a heteroaryl, a cyclic group, a multicyclic group, and/or NR1R2 wherein R1 and R2, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, optionally comprising a spacer or linker between R and B, and or a boronate compound of Formula III:

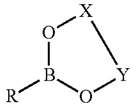

[Formula III], where R in Formula III is independently selected from hydrogen, hydroxyl, an alkyl group, an alkoxy group, an amino group, an aryl group, a heteroaryl, a cyclic group, a multicyclic group, and/or NR1R2 where R1 and R2, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and X and Y=alkyl, where Formula III may optionally include spacer or linker between R and B, or a combination thereof. In some aspects, the spacer or linker between R and B may be independently selected from a C1-C20 linear or branched alkyl or alkoxy. In some aspects, the compound containing boronate or boronic acid moieties may be selected from 2-acrylamidophenylboronic acid, 3-(Acrylamido)phenylboronic acid, 4-vinylboronic acid containing moieties, and (3-methacrylamidophenyl)boronic acid. In some aspects, the compound containing boronate or boronic acid moieties may be provided at a molar ratio of 0.1 to 100 to analyte indicator monomer.

In some aspects, the polymer has a backbone, and the monomer spacer may be covalently linked to the backbone of the polymer. In some aspects, the monomer spacer covalently linked to the backbone of the polymer may include a poly(ethylene), poly(ethylene glycol), poly(vinyl alcohol), poly(pyrrolidone), poly(acrylamide), poly(acrylic acid), or poly(amine) group. In some aspects, the poly (ethylene), poly(ethylene glycol), poly(vinyl alcohol), poly (pyrrolidone), poly(acrylamide), poly(acrylic acid), or poly (amine) group may be covalently linked to an acrylate, methacrylate, acrylamide, or methacrylamide group of the analyte indicator.

In some aspects, the monomer spacer covalently linked to the backbone of the polymer may include a flexible spacer having a repeating group selected from:

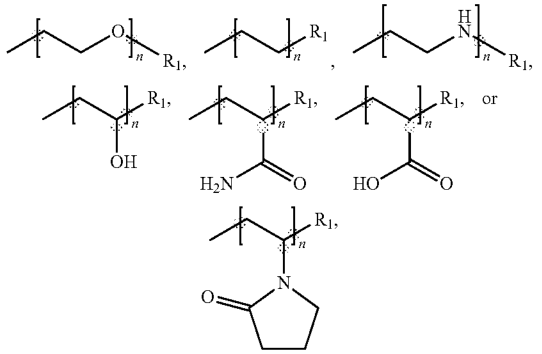

or a combination thereof, wherein R1 is a reactive group and wherein n is 1 to 1000.

In some aspects, the reactive group may be

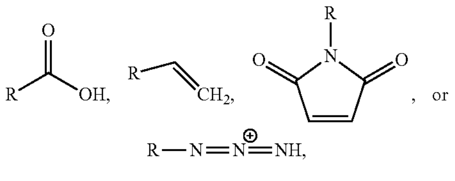

where R is the repeating group.

In some aspects, the ROS scavenger molecules may include

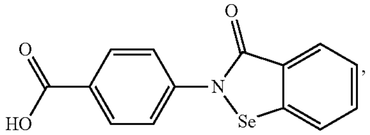

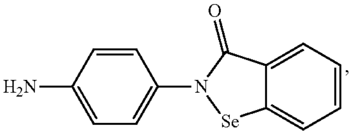

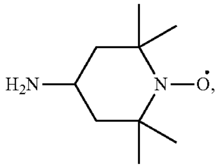 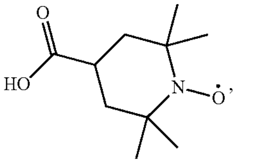

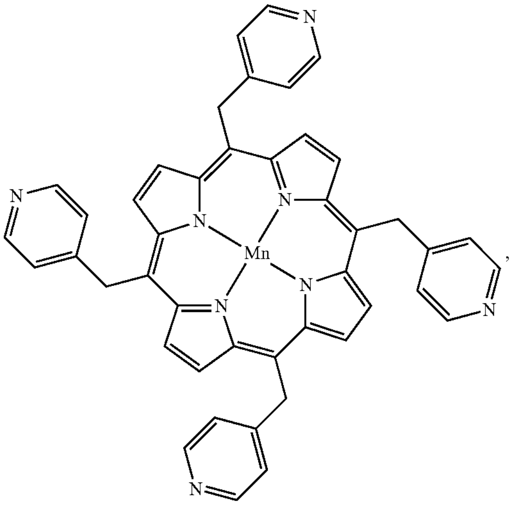

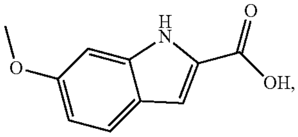

(6-Methoxyindole-2-carboxylic acid)

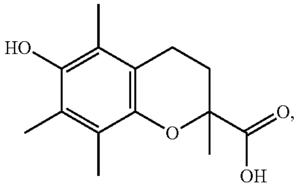

(6-Hydroxy-2,5,7,8-tetramethylchroman-2-carboxylic acid)

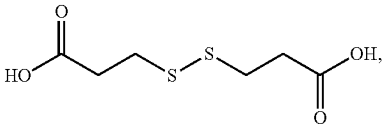

(3,3′-Dithiodipropionic acid)

or a combination thereof. In some aspects, the ROS scavenger molecules may further include a reactive group attached thereto selected from a primary amine, a thiol, or an alkyne group.

In some aspects, the plurality of ROS scavenger molecules may be covalently linked to the monomer spacer molecule via a coupling bond selected from an amide bond, a carbon-thiol bond, a malamide-thiol bond, or a triazole bond. In some aspects, the coupling bond may formed between a reactive group RG1 of the monomer spacer molecule and a reactive group RG2 of the ROS scavenger molecules selected from:

| | $RG_1$ | $RG_2$ | Resulting Bond |
|---|---|---|---|
| a) | 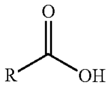 Acid | $H_2N—R$ Primary Amine | 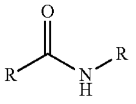 Amide |
| b) | 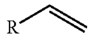 Double Carbon Bond | 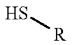 Thiol | 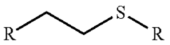 Carbon-Thiol |
| c) | 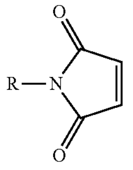 Maleimide | 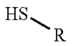 Thiol | 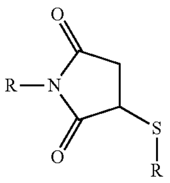 Malamide-Thiol |
| d) | $R—N{=}\overset{\oplus}{N}{=}NH$ Azide |  Alkyne | 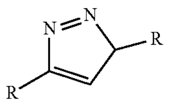 Triazole |

In some aspects, the ROS scavenger molecules may reduce a degradation rate of the analyte indicator. In some aspects, the ROS scavenger molecules may reduce contact of degradative species with the analyte indicator. In some aspects, the degradative species may be hydrogen peroxide, a reactive oxygen species, a reactive nitrogen species, enzymes, free radical or metal ions.

In some aspects, the analyte indicator may resist biofouling by three- to six-fold longer than an analyte indicator not having said ROS scavenger molecules. In some aspects, the ROS scavenger molecules may not interfere with the analyte-binding aspects of the analyte indicator. In some aspects, the ROS scavenger molecules may not interfere with the signaling aspects of the analyte indicator. In some aspects, the ROS scavenger molecules may not leach out of or dissociate from the sensor.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION

Figure 1:
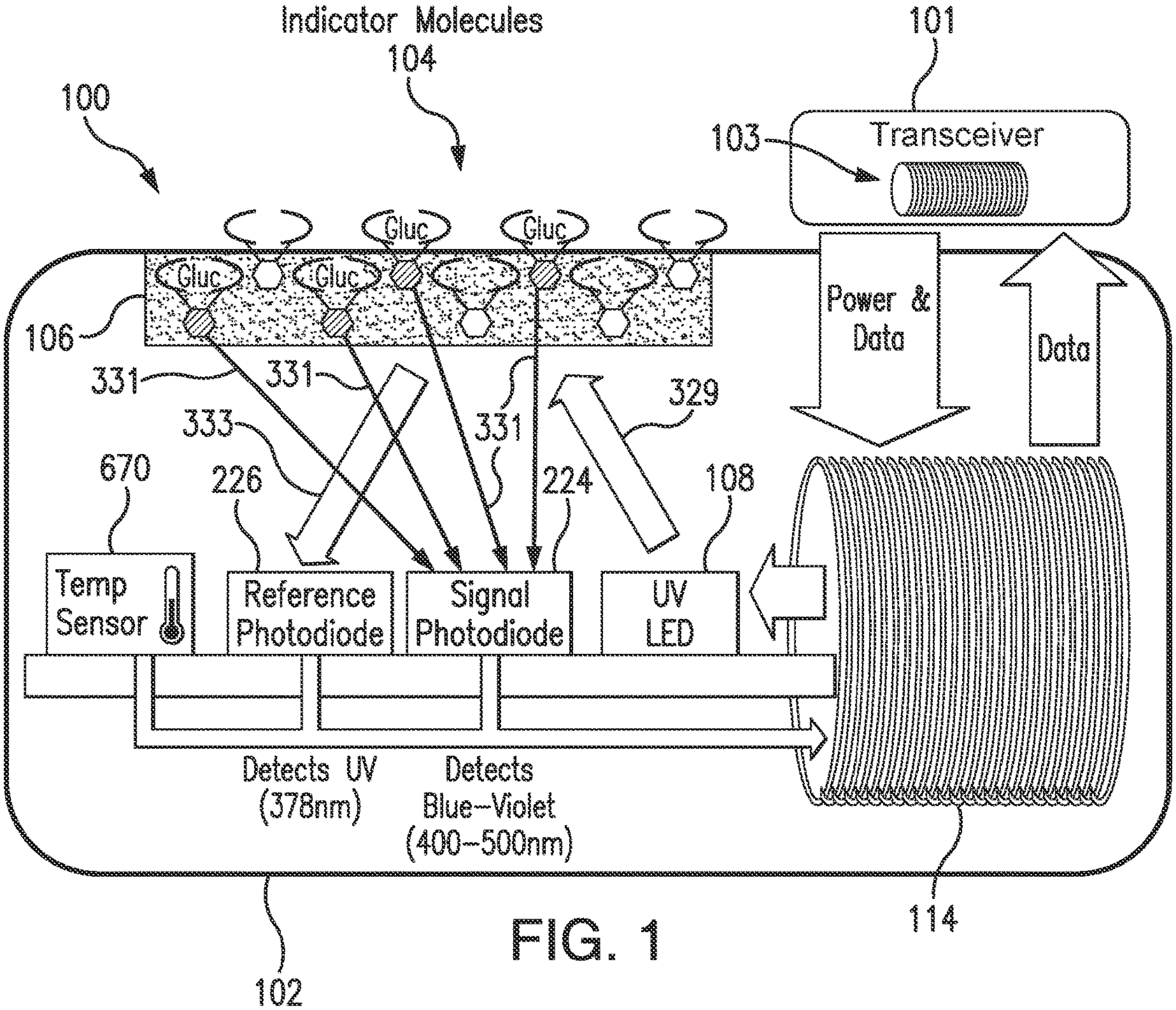
FIG. 1 is a schematic view illustrating a system embodying aspects of the present invention.

FIG. 1 is a schematic view of a system embodying aspects of the present invention. In some non-limiting embodiment, as shown in FIG. 1, the system may include a medical device 100 and an external transceiver 101. In some embodiments, the medical device 100 may be an implantable medical device (IMD). In some embodiments, the medical device 100 may be a sensor. In some embodiments, the medical device 100 may be an implantable sensor configured to be fully or partially implanted in a living animal (e.g., a living human). In some embodiments, the medical device 100 may be implanted, for example, in a living animal's arm, wrist, leg, abdomen, peritoneum, or other region of the living animal suitable for device implantation. For example, in some non-limiting embodiments, the medical device 100 may be implanted beneath the skin (i.e., in the subcutaneous or peritoneal tissues). However, this is not required, and, in some alternative embodiments, the medical device 100 may be a transcutaneous device (e.g., a transcutaneous sensor). In some alternative embodiments, the medical device 100 may not be a sensor and may instead be another type of device (e.g., a pacemaker, stimulator, an implant (e.g., hard or soft tissue mimic such as bone replacement or implant or a breast implant), or delivery device).

In some embodiments, a transceiver 101 may be an electronic device that communicates with the medical device 100 to power the medical device 100, provide commands and/or data to the medical device 100, and/or receive data from the medical device 100. In some embodiments, the received data may include one or more sensor measurements. In some embodiments, the sensor measurements may include, for example and without limitation, one or more light measurements from one or more photodetectors of the medical device 100 and/or one or more temperature measurements from one or more temperature sensors of the medical device 100. In some embodiments, the transceiver 101 may calculate analyte (e.g., glucose) concentrations from the measurement information received from the medical device 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two minutes, and/or upon user initiation) measurement commands (i.e., requests for measurement information) to the medical device 100. In some embodiments where the transceiver 101 is a handheld device, positioning (i.e., hovering or swiping/waving/passing) the transceiver 101 within range over the sensor implant site (i.e., within proximity of the medical device 100) may cause the transceiver 101 to automatically convey a measurement command to the medical device 100 and receive a data from the medical device 100.

In some embodiments, as shown in FIG. 1, the transceiver 101 may include an inductive element 103, such as, for example, a coil. In some embodiments, the transceiver 101 may generate an electromagnetic wave or electrodynamic field (e.g., by using a coil) to induce a current in an inductive element 114 of the medical device 100. In some non-limiting embodiments, the medical device 100 may use the current induced in the inductive element 114 to power the medical device 100. However, this is not required, and, in some alternative embodiments, the medical device 100 may be powered by an internal power source (e.g., a battery).

In some embodiments, the transceiver 101 may convey data (e.g., commands) to the medical device 100. For example, in some non-limiting embodiments, the transceiver 101 may convey data by modulating the electromagnetic wave generated by the inductive element 103 (e.g., by modulating the current flowing through the inductive element 103 of the transceiver 101). In some embodiments, the medical device 100 may detect/extract the modulation in the electromagnetic wave generated by the transceiver 101. Moreover, the transceiver 101 may receive data (e.g., one or more sensor measurements) from the medical device 100. For example, in some non-limiting embodiments, the transceiver 101 may receive data by detecting modulations in the electromagnetic wave generated by the medical device 100, e.g., by detecting modulations in the current flowing through the inductive element 103 of the transceiver 101.

In some embodiments, as shown in FIG. 1, the medical device 100 may include a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, as shown in FIG. 1, the medical device 100 may include an analyte indicator 106. In some non-limiting embodiments, the analyte indicator 106 may be a polymer graft coated, diffused, adhered, or embedded on at least a portion of the exterior surface of the sensor housing 102. The analyte indicator 106 (e.g., polymer graft) may cover the entire surface of sensor housing 102 or only one or more portions of the surface of housing 102. As an alternative to coating the analyte indicator 106 on the outer surface of sensor housing 102, the analyte indicator 106 may be disposed on the outer surface of the sensor housing 102 in other ways, such as by deposition or adhesion. In some embodiments, the analyte indicator 106 may be a fluorescent glucose indicating polymer. In one non-limiting embodiment, the polymer is biocompatible and stable, grafted onto the surface of sensor housing 102, designed to allow for the direct measurement of glucose in interstitial fluid (ISF), blood, or intraperitoneal fluid after implantation of the medical device 100. In some embodiments, the analyte indicator 106 may be a hydrogel.

In some embodiments, the analyte indicator 106 (e.g., polymer graft) of the medical device 100 may include indicator molecules 104. The indicator molecules 104 may be distributed throughout the entire analyte indicator 106 or only throughout one or more portions of the analyte indicator 106. The indicator molecules 104 may have a boronate group. The indicator molecules 104 may be fluorescent indicator molecules (e.g., TFM having the chemical name 9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(carboxyethyl)amino]methyl]anthracene sodium salt) or light absorbing, non-fluorescent indicator molecules. In some embodiments, the indicator molecules 104 may reversibly bind an analyte (e.g., glucose, oxygen, cardiac markers, low-density lipoprotein (LDL), high-density lipoprotein (HDL), or triglycerides). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no analyte is bound, the indicator molecule 104 may be only weakly fluorescent.

Attempts to incorporate ROS scavenging molecules into hydrogel components (e.g., HEMA and PEGDA) by reacting the molecules with the hydrogel monomers produced hydrogels having either drastically different optical properties or caused the ROS scavenging molecules to be entrapped in the bulk of the copolymer network. When the ROS scavenging molecules were entrapped in the bulk of the copolymer network, the result was inaccessible chemistries to ROS, which failed to scavenge ROS.

Further, if the ROS scavenging chemistry is not located directly at the surface of the polymer interfacing the surrounding solution, the ROS will continue to degrade the hydrogel. Further, some antioxidant chemistries are also unable to participate in polymerization processes because the ROS scavenging molecules scavenge the initiator used to react the monomers that form the hydrogel.

In some embodiments, the medical device 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the medical device 100 may also include one or more photodetectors (e.g., photodiodes, phototransistors, photoresistors or other photosensitive elements). For example, in the embodiment illustrated in FIG. 1, medical device 100 has a first photodetector 224 and a second photodetector 226. However, this is not required, and, in some alternative embodiments, the medical device 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the analyte indicator 106 back into the medical device 100 as reflection light 333, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the medical device 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the analyte indicator 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the analyte indicator 106, and, therefore, a greater number of photons striking the first photodetector 224.

In some embodiments, as shown in FIG. 1, the medical device 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of medical device 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the medical device 100 and/or transceiver 101 may be as described in one or more of U.S. application Ser. Nos. 13/761,839, 13/937,871, and 13/650,016.

In some embodiments, the medical device 100 may include a transceiver interface device, and the transceiver 101 may include a sensor interface device. In some embodiments where the medical device 100 and transceiver 101 include an antenna or antennas (e.g., inductive elements 103 and 114), the transceiver interface device may include the inductive element 114 of the medical device 100, and the sensor interface device may include the inductive element 103 of the transceiver 101. In some of the transcutaneous embodiments where there exists a wired connection between the medical device 100 and the transceiver 101, the transceiver interface device and sensor interface device may include the wired connection.

Figure 2:
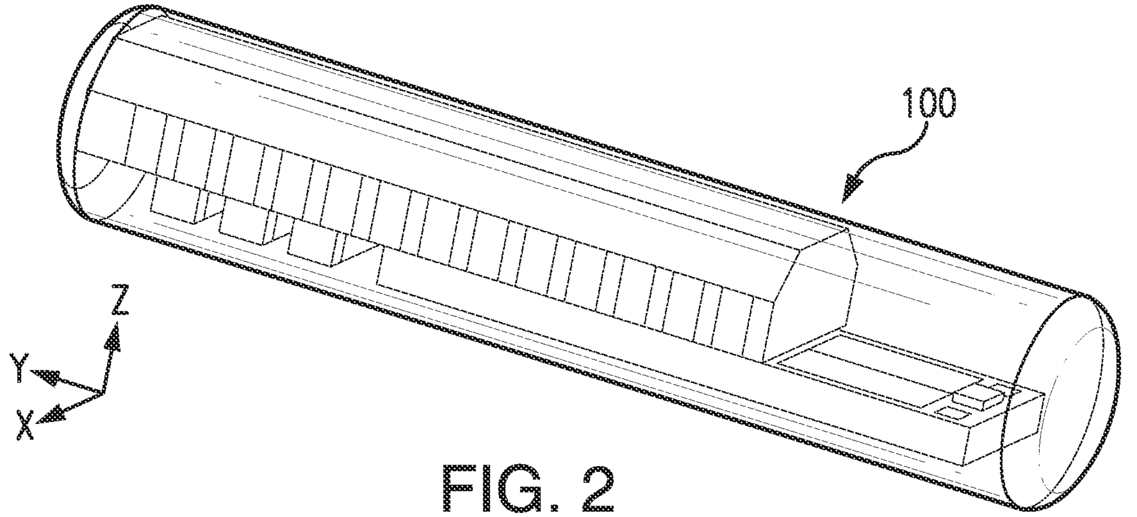
FIG. 2 illustrates a perspective view of a medical device embodying aspects of the present invention.
Figure 3:
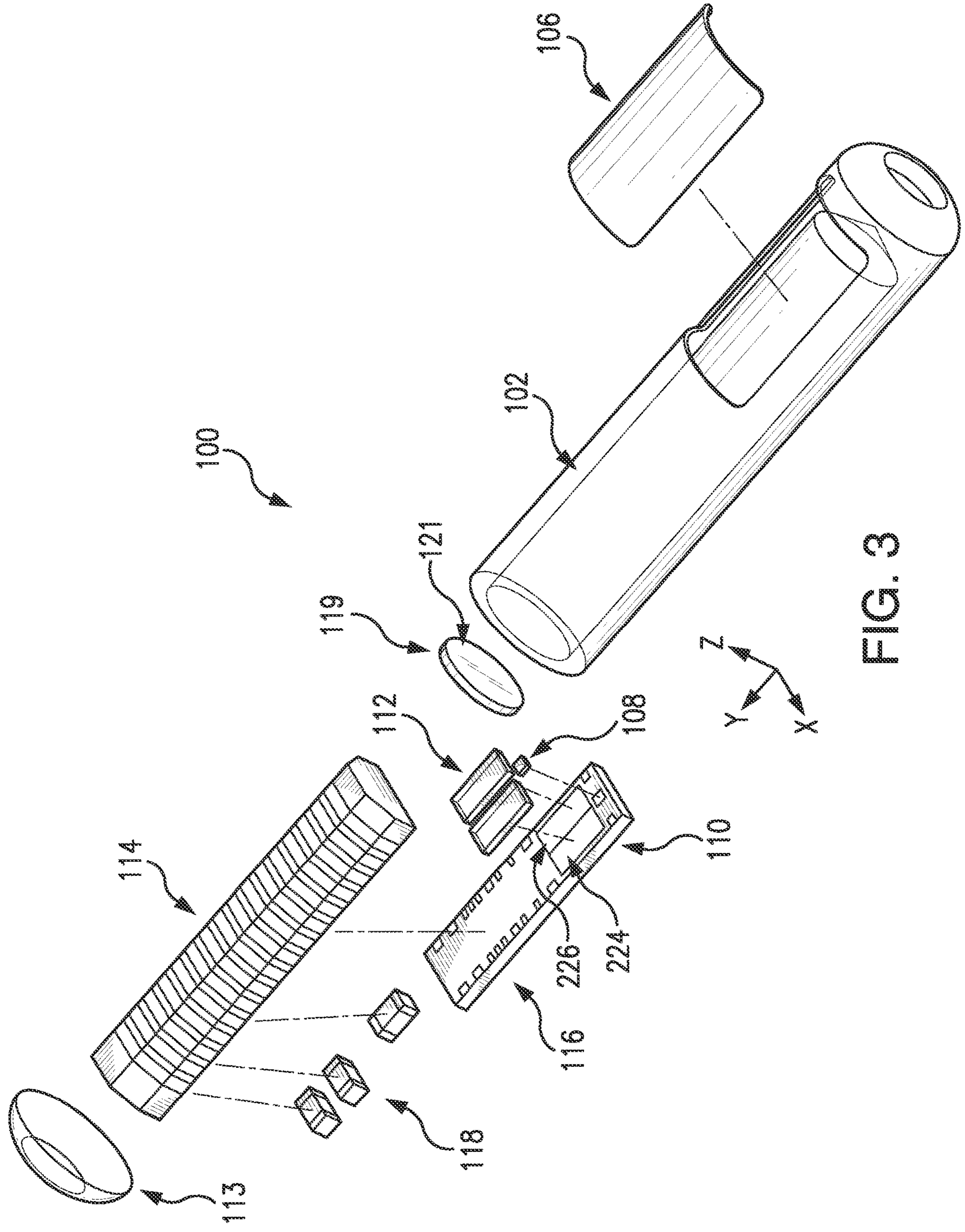
FIG. 3 illustrates an exploded view of a medical device embodying aspects of the present invention.
Figure 4:
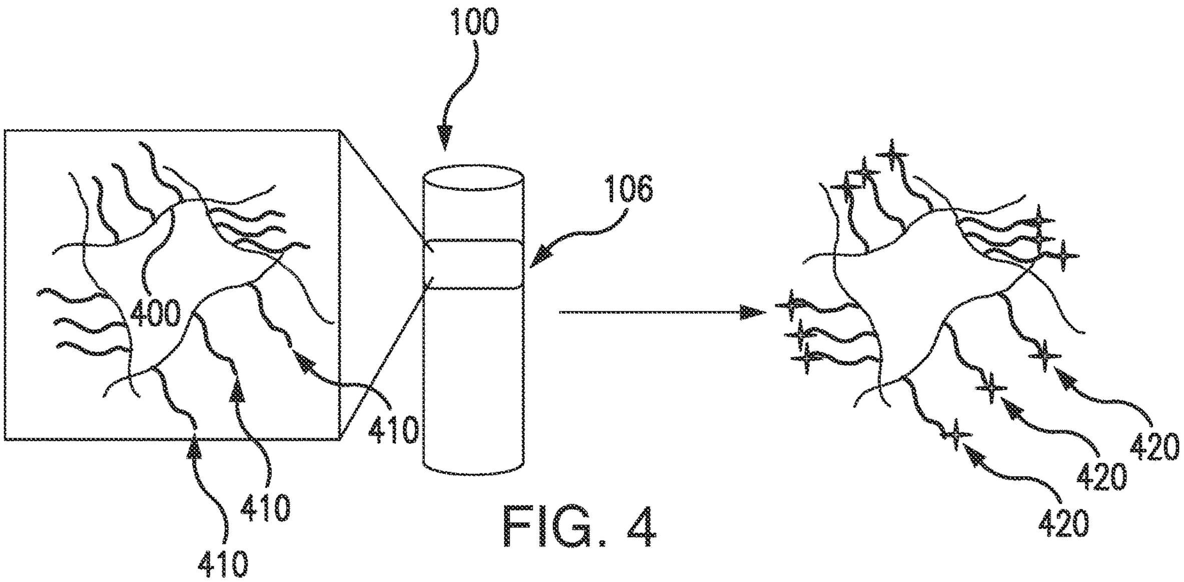
FIG. 4 schematically illustrates a post-graft modification reaction of a polymer graft backbone having a plurality of monomer spacers covalently linked thereto via reactive coupling chemistry to form a polymer graft backbone having reactive oxygen species (ROS) scavenger molecules covalently linked to the polymer graft via the monomer spacers.

FIGS. 2 and 3 illustrate a non-limiting embodiment of a medical device 100 embodying aspects of the present invention that may be used in the sensor system illustrated in FIG. 1. FIGS. 2 and 3 illustrate perspective and exploded views, respectively, of the non-limiting embodiment of the medical device 100 before post-graft modification of the analyte indicator 106 (polymer graft 400) as schematically depicted in FIG. 4.

In some embodiments, as illustrated in FIG. 3, the sensor housing 102 may include an end cap 113. In some embodiments, the medical device 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the medical device 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the medical device 100.

According to one aspect of the invention, an application for which the medical device 100 was developed (although by no means the only application for which it is suitable) is measuring various biological analytes in the living body of an animal (including a human). For example, medical device 100 may be used to measure glucose, oxygen, toxins, pharmaceuticals or other drugs, hormones, and other metabolic analytes in, for example, the human body.

In some embodiments, the specific composition of the analyte indicator 106 and the indicator molecules 104 may vary depending on the particular analyte the sensor is to be used to detect and/or where the sensor is to be used to detect the analyte (e.g., in the in subcutaneous tissues, blood, or peritoneum). In some embodiments, the analyte indicator 106 facilitates exposure of the indicator molecules 104 to the analyte. In some embodiments, the indicator molecules 104 may exhibit a characteristic (e.g., emit an amount of fluorescence light) that is a function of the concentration of the specific analyte to which the indicator molecules 104 are exposed.

In some embodiments, the medical device 100 may include at least one drug eluting polymer matrix and/or a layer of catalyst and/or one or more therapeutic agents that may be provided on, incorporated in, or dispersed within the analyte indicator or sensor housing as described in U.S. Pat. No. 9,931,068 (Huffstetler et al.), which is incorporated herein by reference in its entirety. In some embodiments, the one or more therapeutic agents may be incorporated in the analyte indicator 106. In some embodiments, the medical device 100 may include a membrane covering at least a portion of the analyte indicator 106, and the one or more therapeutic agents may be incorporated within the membrane. In some embodiments, the one or more therapeutic agents include dexamethasone, triamcinolone, betamethasone, methylprednisolone, beclometasone, fludrocortisone, derivatives thereof, and analogs thereof, a glucocorticoid, an anti-inflammatory drug, e.g., a non-steroidal anti-inflammatory drug including but not limited to acetylsalicylic acid, isobutylphenylpropanoic acid.

The implantation or insertion of a medical device, such as a bio-sensor, into a user/patient's body can cause the body to exhibit adverse physiological reactions that are detrimental to the functioning of the device. The reactions may range from infections due to implantation surgery to the immunological response of a foreign object implanted in the body. That is, the performance of the implantable bio-sensor can be hindered or permanently damaged in vivo via the immunological response to an infection or the device itself. In particular, the performance of the analyte indicator 106 may be deteriorated by the immunological response of the body into which the medical device 100 is implanted. For example, as explained above, white blood cells, including neutrophils, may attack an implanted medical device 100. The neutrophils release, inter alia, hydrogen peroxide, which may degrade indicator molecules 104 (e.g., by oxidizing a boronate group of an indicator molecule 104 and disabling the ability of the indicator molecule 104 to bind glucose). Further, proteins, macrophages, and other types of cells and cellular materials may attach to, react with, or be absorbed by the analyte indicator 106 leading to immunogenicity, biofouling, and reduced biocompatibility. Further, in some aspects, infection and bacterial colonization on the analyte indicator 106 may require the implanted medical device 100 to be removed.

According to the present disclosure, the analyte indicator 106 may include a polymer graft backbone 400 as depicted in FIG. 4. As shown in FIG. 4, a plurality of monomer spacers 410 may be covalently linked to the polymer graft backbone 400. In some aspects, the plurality of monomer spacers 410 may be covalently linked to the polymer graft backbone 400 in a spaced apart pattern. In some aspects, the spaced apart pattern may be uniformly spaced or non-uniformly spaced.

In some aspects, each of the monomer spacers 410 may independently include a poly(ethylene), poly(ethylene glycol), poly(vinyl alcohol), poly(pyrrolidone), poly(acrylamide), poly(acrylic acid), or poly(amine) group. In some aspects, each of the poly(ethylene), poly(ethylene glycol), poly(vinyl alcohol), poly(pyrrolidone), poly(acrylamide), poly(acrylic acid), or poly(amine) group may be covalently linked to an acrylate, methacrylate, acrylamide, or methacrylamide group of the polymer graft 400. In some aspects, each of the monomer spacers 410 may independently further include a flexible spacer having a repeating group selected from:

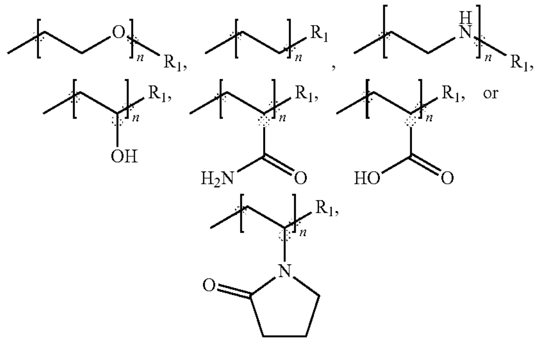

or a combination thereof, wherein $R_1$ is a reactive group and wherein n is 1 to 1000. In some aspects, the reactive group may be an acid, an ene group, a malamide group, an azide group, or any other suitable reactive group for forming coupling chemistry. In some aspects, the reactive group may be

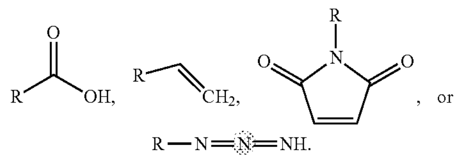

As shown in FIG. 4, the monomer spacers 410 undergo a post-graft modification. As used herein, the term "post-graft modification" refers to a coupling reaction that occurs after the polymer graft 400 has already been synthesized on the medical device 100. Once the polymer graft 400 has already been synthesized on the medical device 100 reactive groups on the monomer spacers 410 are coupled with reactive groups on ROS scavenger molecules 420 to covalently couple the ROS scavenger molecules 420 to the polymer graft 400 backbone via the monomer spacers 410.

Figure 5:
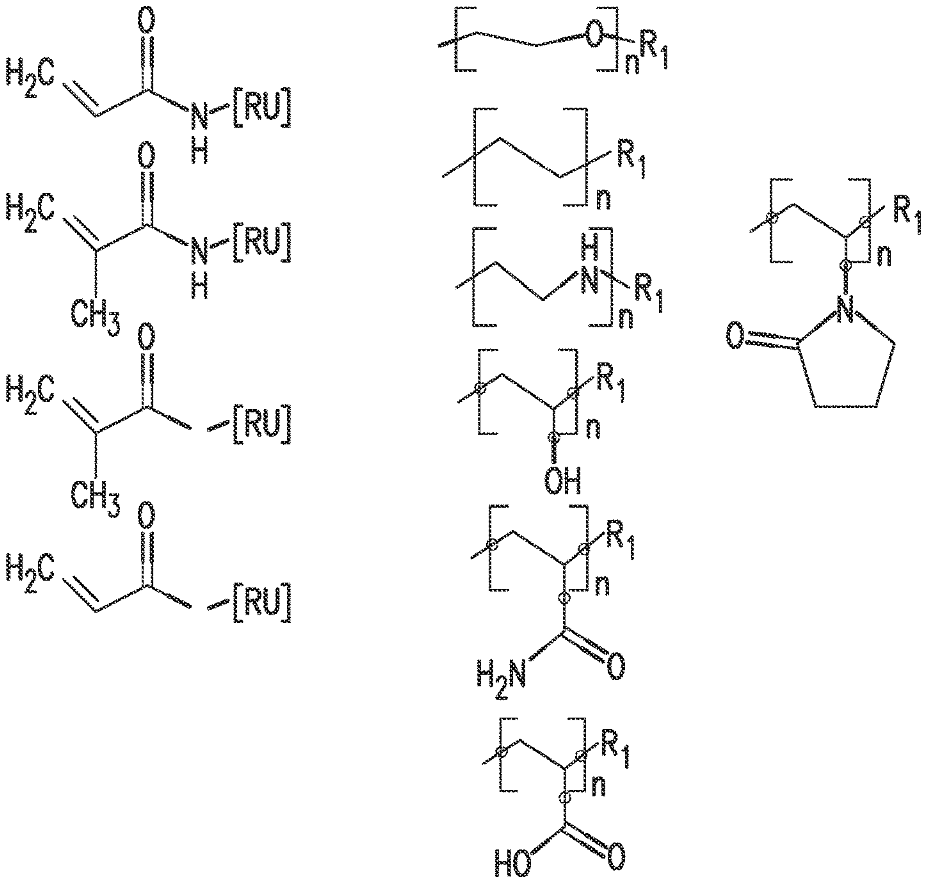
FIG. 5 depicts exemplary monomer spacers for use according to the present disclosure (left) and exemplary repeating units (RUs) for use in the monomer spacer molecules (right).

FIG. 5 depicts exemplary monomer spacers for use according to the present disclosure (left) and exemplary repeating units (RUs) for use in the monomer spacer molecules (right). The ROS scavenger molecules 420 may include one or more of the chemical compounds shown in FIG. 6 or derivatives thereof or any of the ROS scavenger molecules described herein. In some aspects, ROS scavenger molecules 420 may include one or more of the following:

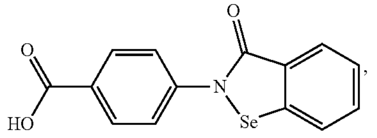

(ebselen carboxylic acid)

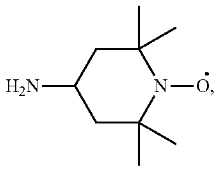

(4-carboxy TEMPO)

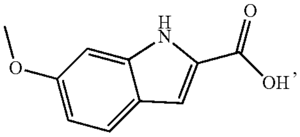

(6-Methoxyindole-2-carboxylic acid)

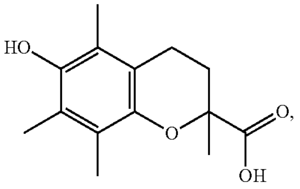

(6-Hydroxy-2,5,7,8-tetramethylchroman-2-carboxylic acid)

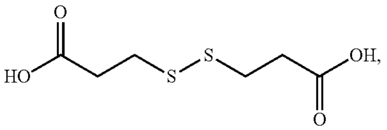

(3,3′-Dithiodipropionic acid)

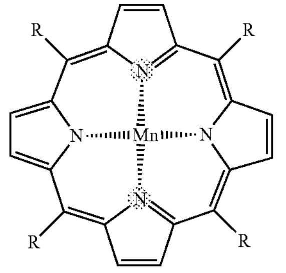

(porphyrin), or a combination thereof, wherein R is

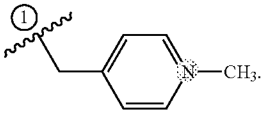

Figure 6:
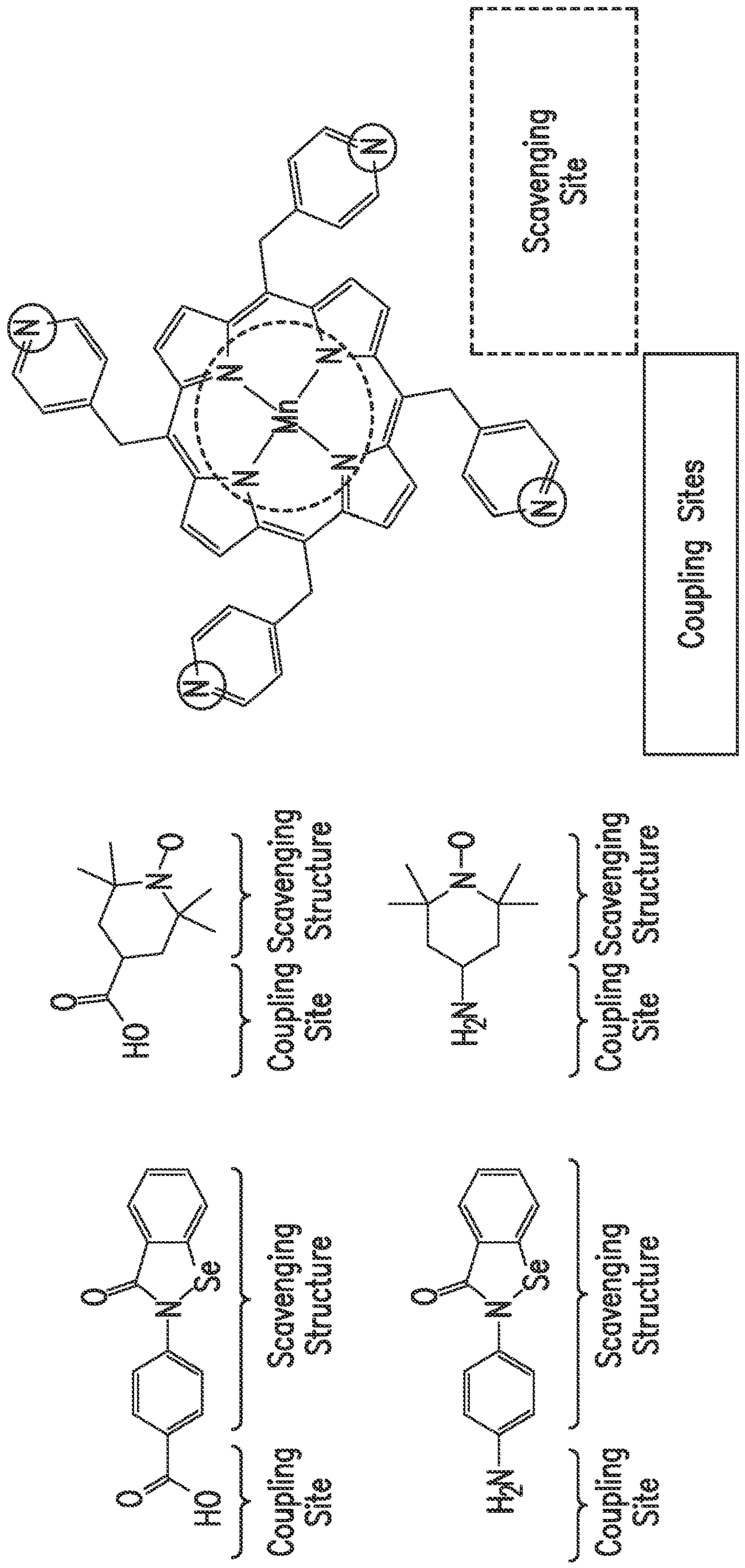
FIG. 6 depicts exemplary reactive oxygen species (ROS) scavenger molecules.
Figure 7:
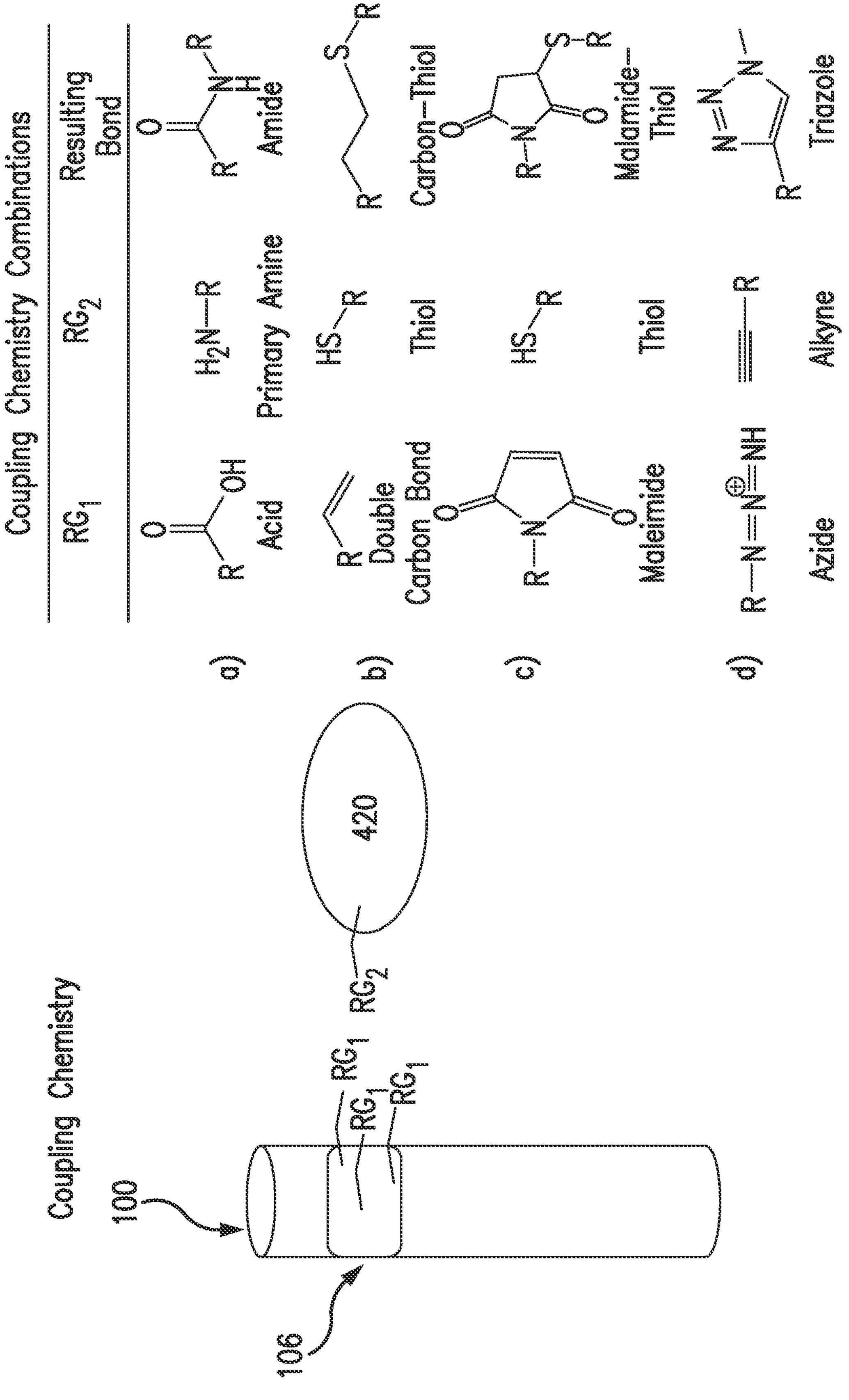
FIG. 7 schematically illustrates a medical device having an analyte indicator (polymer graft) with monomer spacers having reactive groups ($RG_1$s) covalently linked thereto coupling with an exemplary ROS scavenger molecule having a reactive group ($RG_2$) covalently linked thereto (left) and exemplary $RG_1$ and $RG_2$ groups and the types of coupling bonds formed thereby (right).

Reactive groups on the ROS scavenger molecules 420 may be selected from an amine, a thiol group, an alkyne group, carboxylic acid functional groups, or any other suitable reactive group for forming coupling chemistry as shown in FIG. 6 and FIG. 7. FIG. 7 schematically illustrates a medical device 100 having an analyte indicator 106 (polymer graft) with monomer spacers having reactive groups ($RG_1$s) covalently linked thereto coupling with an exemplary ROS scavenger molecule 420 having a reactive group ($RG_2$) covalently linked thereto (left). FIG. 7 also provides exemplary $RG_1$ and $RG_2$ groups and the types of coupling bonds formed through coupling chemistry according to the present disclosure (right). Accordingly, after synthesis of the analyte indicator 106 having a polymer graft backbone 400 having monomer spacers 410 covalently bound thereto on a medical device 100, the polymer graft is then modified by a post-graft coupling reaction with the reactive groups of ROS scavenger molecules to covalently couple the ROS scavenger molecules to the distal ends of monomer spacers. As used herein, "distal ends" refers to the terminal portion of a monomer spacer molecule opposite the covalent bond between the monomer spacer 410 and the polymer graft backbone 400. Thus, as shown in FIG. 4, the ROS scavenger molecules 420 are provided at the distal ends of the monomer spacers 410 to be surface accessible and thereby be available to react with degradative species in the environment of the medical device 100 and prevent, inhibit, or reduce degradation of the analyte indicator 106 by degradative species.

In some aspects, the coupled ROS scavenger molecules 420 prevent, inhibit, or reduce such degradative phenomena (e.g., interactions, attachments, absorption, and colonization) with one or more degradative species without compromising signal integrity or performance of the sensor device. The degradative species may include one or more of proteins, peptides, cells, macrophages, bacteria, hydrogen peroxide, a reactive oxygen species, a reactive nitrogen species, a free radical, enzymes, and a metal ion.

In some non-limiting embodiments, a medical device 100 for measurement of an analyte (e.g., glucose) in a medium (e.g., interstitial fluid) within a living animal (e.g., a human) contains one or more of the following components: a sensor housing 102; a light source 108 within the sensor housing 102 configured to emit excitation light 329; an analyte indicator 106 covering a portion of the sensor housing 102; one or more indicator molecules 104 that are part of the analyte indicator 106, reversibly bind the analyte, are positioned to be irradiated by the excitation light, and are configured to emit light 331 indicative of the amount of the analyte in the medium within the living animal; a photodetector 224 within the sensor housing 102 that is sensitive to light 331 emitted by the one or more indicator molecules 104 and configured to generate a signal indicative of the amount of the analyte in the medium within the living animal; and a plurality of ROS scavenger molecules 420 covalently linked to monomer spacers 410 via a coupling bond, wherein the monomer spacers 410 are covalently bound to the polymer graft backbone 400 of the analyte indicator 106, wherein the ROS scavenger molecules 420 interact with degradative species without compromising signal integrity or performance of the medical device 100. In some non-limiting embodiments, the medical device 100 may include a drug eluting matrix and/or a layer of catalyst provided on or incorporated in the analyte indicator 106.

In some non-limiting embodiments, the one or more of the compounds containing boronate or boronic acid containing moieties may be a boronic acid compound of Formula I: R—B$(OH)_2$ [Formula I]. In some embodiments, R is selected from hydrogen, hydroxyl, an alkyl group, an alkoxy group, an amino group, an aryl group, a heteroaryl, a cyclic group, a multicyclic group, and/or $NR_1R_2$. Further, a spacer or linker may be provided between R and B in Formula I. For example, the spacer or linker may be a $C_1$-$C_{20}$ linear or branched alkyl or alkoxy. In some embodiments, $R_1$ and $R_2$ may be identical or different and each may represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group.

In some non-limiting examples, the one or more boronic acid containing moieties compounds may include one or more of the following phenylboronic acid containing compound:

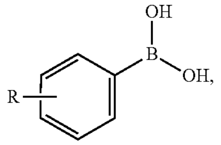

wherein one or more R may be independently selected from hydrogen, hydroxyl, an alkyl group, an alkoxy group, an amino group, an aryl group, a heteroaryl, a cyclic group, a multicyclic group, and/or $NR_1R_2$. Further, a spacer or linker may be provided between R and B in Formula I. For example, the spacer or linker may be a $C_1$-$C_{20}$ linear or branched alkyl or alkoxy. In some embodiments, $R_1$ and $R_2$ may be identical or different and each may represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group. In some non-limiting examples, the one or more boronic acid containing moieties compounds may include one or more of the following compounds:

ORTHO

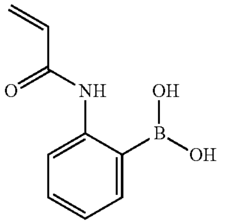

2-Acrylamidophenyliboronic acid

META

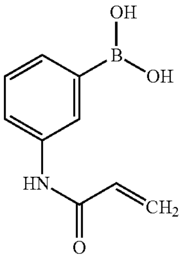

3-(Acrlyamido)phenylboronic acid

PARA

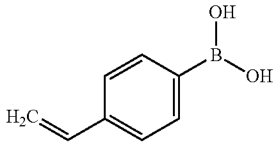

4-Vinylphenylboronic acid

-continued

META-METHYL

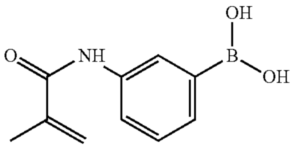

(3-Methacrylamidophenyl)boronic acid

In some non-limiting embodiments, one or more of the compounds containing boronate or boronic acid containing moieties may be a boronate compound of Formula II:

[Formula II]

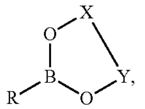

wherein R is independently selected from hydrogen, hydroxyl, an alkyl group, an alkoxy group, an amino group, an aryl group, a heteroaryl, a cyclic group, a multicyclic group, and/or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and wherein X and Y=alkyl. Further, a spacer or linker may be provided between R and B in Formula II. For example, the spacer or linker may be a $C_1$-$C_{20}$ linear or branched alkyl or alkoxy.

In some non-limiting embodiments, one or more compounds containing boronate or boronic acid containing moieties may be provided as co-monomers of four monomers according to Formula III: ABC [Formula III], wherein A is a methacrylate monomer, B is a polyethylene glycol monomer, and C is a boronate or boronic acid containing moiety compound monomer, wherein A is 1 to 99% by weight, B is 1 to 99% by weight, and C is 0.001 to 99% by weight of the total polymer.

In some embodiments, the PEG may be polyethylene glycol methacrylate (PEG-methacrylate) or polyethylene glycol diacrylate (PEG-diacrylate or PEGDA), and the boronate or boronic acid containing moieties monomer of Formula I may be methacrylate-containing phenyl boronic acid or boronate-containing moieties. In some embodiments, the monomers may be in specific molar ratios. For example, in some non-limiting embodiments in which the analyte indicator 106 is opaque, HEMA may comprise 10 to 90 molar percent, PEGDA may comprise 10 to 90 molar percent, and the methacrylate-containing phenyl boronic acid or boronate-containing moieties may comprise 0.001 to 90 molar percent.

In some embodiments, the PEGDA may act as a cross-linker and create a sponge-like matrix/hydrogel. In some non-limiting embodiments, the PEG-containing graft/hydrogel may become clear if a sufficient amount of additional PEG is added to the mixture (i.e., if it is fabricated with a higher concentration of PEG), and a clear hydrogel may be made from such a formulation. For example, in one non-limiting embodiment, the hydrogel may be made using a polymer solution that is 50-60% water by volume and 40-50% monomers by volume, where the HEMA, PEG-methacrylate, and the compound containing boronate or boronic acid containing moieties may comprise 0.01 to 10%, 1 to 99%, 1 to 99%, and 0.01 to 99% by weight, of the monomers in the solution. In some embodiments, the polymer graft may be synthesized using conventional free radical polymerization.

According to one objective of the present disclosure, the presence of the plurality of reactive oxygen species (ROS) scavenger molecules 420 covalently linked to the analyte indicator 106 via monomer spacers 410 does not alter the glucose recognition properties of the medical device 100. In some aspects, the monomer spacers are flexible and hydrophilic.

An implanted sensor including a plurality of reactive oxygen species (ROS) scavenger molecules 420 covalently linked to the analyte indicator 106 via monomer spacers 410 may have improved performance over a sensor that does not include the plurality of reactive oxygen species (ROS) scavenger molecules. For instance, in some non-limiting embodiments, the plurality of reactive oxygen species (ROS) scavenger molecules 420 covalently linked to the analyte indicator 106 via monomer spacers 410 may improve the longevity and functionality of the medical device 100. In some aspects, a sensor according to the present disclosure having the plurality of reactive oxygen species (ROS) scavenger molecules 420 covalently linked to the analyte indicator 106 via monomer spacers 410 has an increased longevity, e.g., a four-fold increased longevity. For example, in a sensor having an analyte sensor containing analyte indicator 106 without a plurality of reactive oxygen species (ROS) scavenger molecules 420 covalently linked to the analyte indicator 106 via monomer spacers 410, a sensor longevity of 90 days may be expected. However, after using an analyte sensor containing analyte indicator 106 in combination with a plurality of reactive oxygen species (ROS) scavenger molecules 420 covalently linked to the analyte indicator 106 via monomer spacers 410 according to the present disclosure, a sensor longevity of about 240-360 days or longer may be achieved. As another example, in a sensor having analyte indicator 106, a sensor longevity of 120 days may be expected. However, after using an analyte sensor containing analyte indicator 106 in combination with a plurality of reactive oxygen species (ROS) scavenger molecules 420 covalently linked to the analyte indicator 106 via monomer spacers 410 according to the present disclosure, a sensor longevity of up to 480 days may be achieved.

Synthetic Procedure: An acrylate poly(ethylene glycol) amine (molecular weight 1000-5000 Daltons) was dissolved an aqueous solution at a concentration of 0.003-1 g per mL. Other monomers to serve as mechanical reinforcement such as acrylamide, (hydroxyethyl)methacrylate, acrylate poly (ethylene glycol), N,N'-Methylenebisacrylamide, and poly (ethylene diacrylate) can be dissolved between 0.25-1 g per mL. A thermal initiator, such as VAZO 44, is dissolved in the monomer solution anywhere between 0.1-1 mg per mL. The monomer and initiation solution can be dissolved in aqueous buffer with acidic, neutral, or basic pH. Polymerization can be performed between 40 and 65° C. for 0.5 to 5 hours.

To append a carboxylic acid catalytic molecule of interest, it should be dissolved in 0.1M 2-(N-morpholino)ethanesulfonic acid buffer with a pH between 4 and 5. The carboxylic acid terminated catalytic molecule can be dissolved between 0.1 and 50 mM. The solution should be stirred for 15-30 minutes to ensure proper dissolution of the catalytic molecule. 1-Ethyl-3-[3-dimethylaminopropyl]carbodiimide hydrochloride (EDC) and N-hydroxysuccinimide (NHS) should be added excess to that of the carboxylic acid (Ex: EDC 0.5 mM and NHS 1 mM for 0.1 mM carboxylic acid solutions; EDC 100 and NHS 200 mM for 50 mM carboxylic acid solutions). The carboxylic acid and coupling reagents should mix for 15-30 minutes using a shaker or stir plate on medium-high settings. The solution pH must be brought up to neutral with IN sodium hydroxide after the carboxylic acid/EDC/NHS reaction to ensure proper coupling to nucleophiles (primary amines, and hydroxyl functional groups). The hydrogel should be completely submerged in the carboxylic acid/EDC/NHS neutral pH solution for adequate coupling to the surface accessible amines or hydroxyls. Once submerged, the coupling reaction should be placed on a shaker with medium-low settings for four hours. After the reaction is complete, the hydrogel should be rinsed of excess solution and placed in an aqueous buffer (phosphate buffer saline for example) to remove any unbound carboxylic acid or coupling reagents.

Figure 8A:
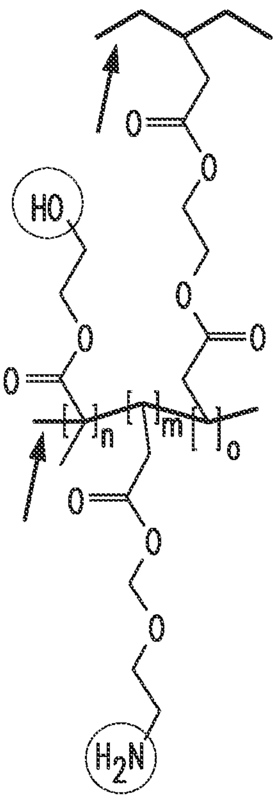
FIG. 8A illustrates the polymer chemical structure, and arrows indicate where carbon bonds are the backbone of the molecule.
Figure 8B:
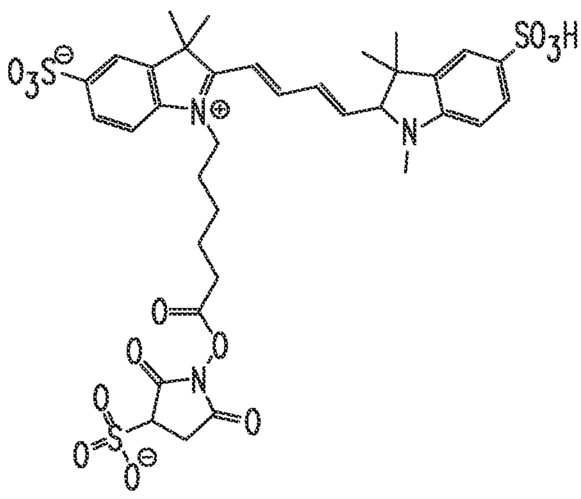
FIG. 8B illustrates the dye carboxylic acid for which the hydroxyl and primary amine groups highlighted in FIG. 8A are the intended targets.
Figure 8C:
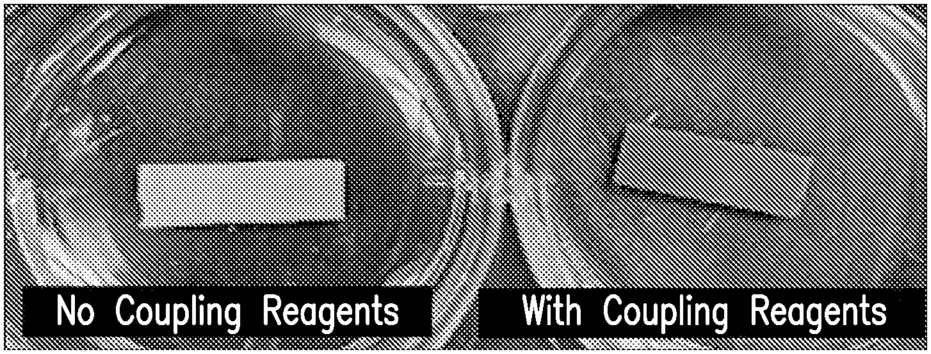
FIG. 8C is an image of the hydrogel made with HEMA, PEGDA, and Acrylate PEG Amine conjugated with dye carboxylic and a control with no coupling reagents on the left side and successful conjugation of the dye on the right side.
Figure 8D:
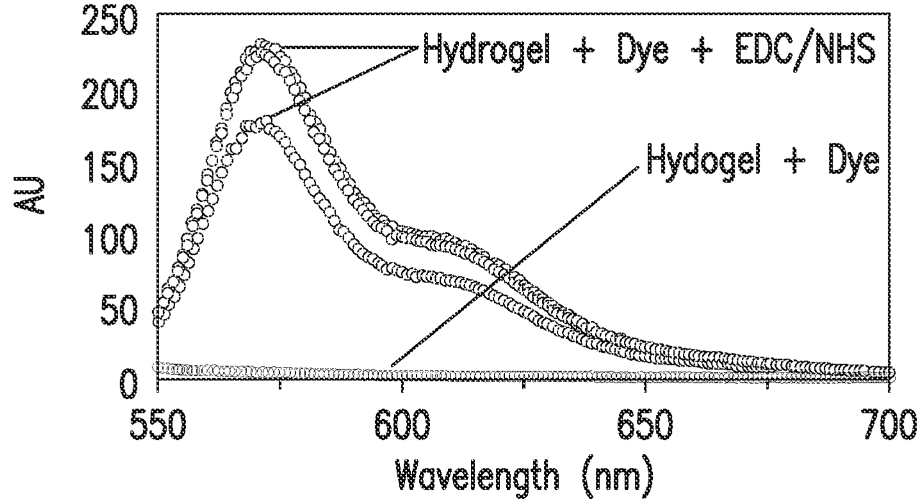
FIG. 8D illustrates the fluorescent spectra of hydrogel films that were treated with dye and coupling reagents EDC/NHS, and dye with no coupling reagents and three replicates for each treatment type.

FIG. 8A illustrates the polymer chemical structure, and arrows indicate where carbon bonds are the backbone of the molecule. FIG. 8B illustrates the dye carboxylic acid for which the hydroxyl and primary amine groups highlighted in FIG. 8A are the intended targets. FIG. 8C is an image of the hydrogel made with HEMA, PEGDA, and Acrylate PEG Amine conjugated with dye carboxylic and a control with no coupling reagents on the left side and successful conjugation of the dye on the right side. FIG. 8D illustrates the fluorescent spectra of hydrogel films that were treated with dye and coupling reagents EDC/NHS, and dye with no coupling reagents and three replicates for each treatment type.

Thus, an analyte indicator 106 in combination with a plurality of reactive oxygen species (ROS) scavenger molecules 420 covalently linked to the analyte indicator 106 via monomer spacers 410 according to the present disclosure may significantly increase sensor longevity and functionality.

Some embodiments may relate to a method of fabricating a medical device 100. In some embodiments, the method may include a first step of disposing a polymer on a surface of the medical device 100. In some embodiments, the medical device 100 may be a sensor for measurement of an analyte in a medium within a living animal. In some embodiments, disposing the polymer on the surface of the medical device 100 may include applying an analyte indicator 106 to a sensor housing 102 of the sensor such that the applied analyte indicator 106 covers at least a portion of the sensor housing 102. In some embodiments, the analyte indicator 106 may include the polymer. In some embodiments, the polymer (e.g., the polymer of the analyte indicator 106) may include co-monomers of at least monomers of A) an analyte indicator monomer, B) at least one monomer selected from an acrylate, methacrylate, acrylamide, or methacrylamide having a monomer spacer 410 and a reactive group at an end thereof, and C) a polyethylene glycol monomer.

In some embodiments, the method may include a second step of coupling a plurality of reactive oxygen species (ROS) scavenger molecules 420 covalently to the polymer. In some embodiments, the second step may be performed after the polymer is disposed on the surface of the medical device 100 in the first step. However, this is not required, and, in some alternative embodiments, the second step may be performed before the polymer is disposed on the surface of the medical device 100 in the first step. In some embodiments, coupling the plurality of ROS scavenger molecules 420 covalently to the polymer in the second step may include coupling the plurality of ROS scavenger molecules 420 covalently to the reactive group of the analyte indicator 106 such that each of the plurality of ROS scavenger molecules 420 is covalently linked to the analyte indicator 106 via the monomer spacer 410.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although in some analyte sensor embodiments, the medical device 100 may be an optical sensor, this is not required, and, in one or more alternative embodiments, the analyte sensor may be a different type of analyte sensor, such as, for example, an electrochemical sensor, a diffusion sensor, or a pressure sensor. Also, although in some embodiments, the medical device 100 may be an implantable sensor, this is not required, and, in some alternative embodiments, the medical device 100 may be a transcutaneous sensor having a wired connection to an external transceiver. For example, in some alternative embodiments, the medical device 100 may be located in or on a transcutaneous needle (e.g., at the tip thereof). In these embodiments, instead of wirelessly communication using an antenna (e.g., inductive element 114), the medical device 100 may communicate with the external transceiver using one or more wires connected between the external transceiver and a transceiver transcutaneous needle including the analyte sensor. For another example, in some alternative embodiments, the medical device 100 may be located in a catheter (e.g., for intravenous blood glucose monitoring) and may communicate (wirelessly or using wires) with an external transceiver.

What is claimed is:

1. A sensor for measurement of an analyte in a medium within a living animal comprising:

a sensor housing;

an analyte indicator covering at least a portion of the sensor housing, and the analyte indicator comprises a polymer; and a plurality of reactive oxygen species (ROS) scavenger molecules covalently linked to the polymer, wherein the ROS scavenger molecules comprise

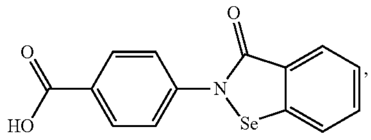
,
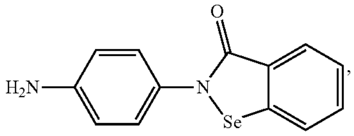
,
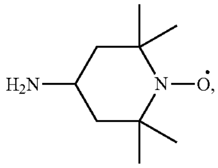
,
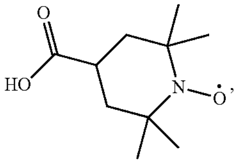
,

-continued

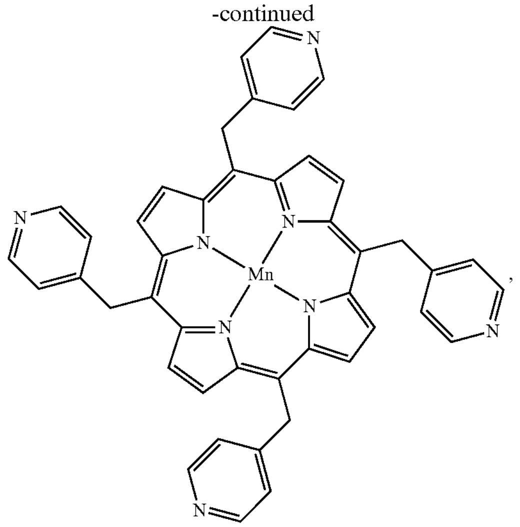

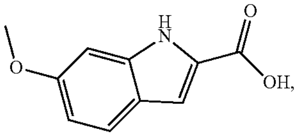

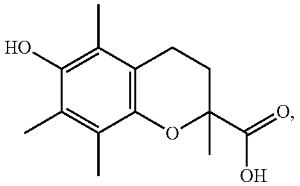

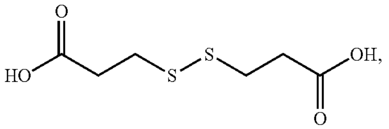

or a combination thereof.

2. The sensor of claim 1, wherein each of the plurality of reactive oxygen species (ROS) scavenger molecules is covalently linked to the polymer via a monomer spacer molecule attached to the polymer.

3. The sensor of claim 2, wherein the polymer has a backbone, and the monomer spacer is covalently linked to the backbone of the polymer.

4. The sensor of claim 3, wherein the polymer comprises co-monomers of at least monomers according to Formula Ia: ABC [Formula Ia], wherein A is an analyte indicator monomer, B is a acrylate, methacrylate, acrylamide, or methacrylamide monomer, C is a polyethylene glycol monomer, wherein A is 0.01 to 10% by weight, B is 1 to 99% by weight, and C is 1 to 99% by weight of Formula Ia.

5. The sensor of claim 3, wherein the polymer comprises co-monomers of four monomers according to Formula Ia: ABCD [Formula Ia], wherein A is an analyte indicator monomer, B is a acrylate, methacrylate, acrylamide, or methacrylamide monomer, C is a polyethylene glycol monomer, D is a compound or a monomer containing boronate or boronic acid moieties, wherein A is 0.01 to 10% by weight, B is 1 to 99% by weight, C is 1 to 99% by weight, and D is 0.01 to 99% by weight of Formula Ia.

6. The sensor of claim 5, wherein the compound or the monomer containing boronate or boronic acid moieties is selected from the group consisting of: a compound of formula II:

R—$B(OH)_2$ [Formula II], wherein R in Formula II is a hydrogen, hydroxyl, an alkyl group, an alkoxy group, an amino group, an aryl group, a heteroaryl, a cyclic group, a multicyclic group, or $NR_1R_2$, wherein $R_1$ and $R_2$ are identical or different and each represents a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, wherein Formula II optionally comprises spacer or linker between R and B, a phenylboronic acid compound

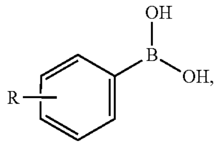

wherein one or more R in the phenylboronic acid compound is independently a hydrogen, hydroxyl, an alkyl group, an alkoxy group, an amino group, an aryl group, a heteroaryl, a cyclic group, a multicyclic group, or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, optionally comprising a spacer or linker between R and B, a boronate compound of Formula III:

[Formula III]

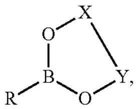

wherein R in Formula III is independently a hydrogen, hydroxyl, an alkyl group, an alkoxy group, an amino group, an aryl group, a heteroaryl, a cyclic group, a multicyclic group, or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and wherein X and Y=alkyl, wherein Formula III optionally comprises spacer or linker between R and B, and a combination thereof.

7. The sensor of claim 6, wherein the spacer or linker between R and B is a $C_1$-$C_{20}$ linear or branched alkyl or alkoxy.

8. The sensor of claim 5, wherein the compound containing boronate or boronic acid moieties is selected from the group consisting of: 2-acrylamidophenylboronic acid, 3-(Acrylamido)phenylboronic acid, 4-vinylboronic acid containing moieties, and (3-methacrylamidophenyl)boronic acid.

9. The sensor of claim 3, wherein the monomer spacer covalently linked to the backbone of the polymer comprises a poly(ethylene), poly(ethylene glycol), poly(vinyl alcohol), poly(pyrrolidone), poly(acrylamide), poly(acrylic acid), or poly(amine) group.

10. The sensor of claim 9, wherein the poly(ethylene), poly(ethylene glycol), poly(vinyl alcohol), poly(pyrrolidone), poly(acrylamide), poly(acrylic acid), or poly(amine) group is covalently linked to an acrylate, methacrylate, acrylamide, or methacrylamide group of the polymer.

11. The sensor of claim 3, wherein the monomer spacer covalently linked to the backbone of the polymer comprises a flexible spacer having a repeating group selected from the group consisting of:

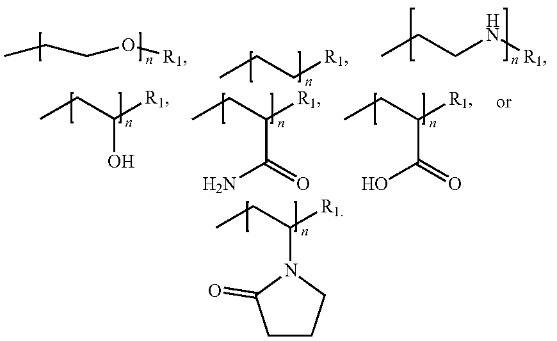

and a combination thereof, wherein $R_1$ is a reactive group and wherein n is 1 to 1000.

12. The sensor of claim 11, wherein the reactive group is

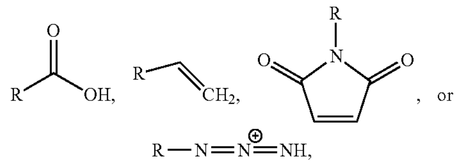

wherein R is the repeating group.

13. The sensor of claim 1, wherein the ROS scavenger molecules further comprise a reactive group attached thereto, wherein the reactive group is a primary amine, a thiol, or an alkyne group.

14. The medical device sensor of claim 2, wherein the plurality of ROS scavenger molecules are covalently linked to the monomer spacer molecule via a coupling bond selected from an amide bond, a carbon-thiol bond, a malamide-thiol bond, or a triazole bond.

15. The sensor of claim 14, wherein the coupling bond is formed between a reactive group $RG_1$ of the monomer spacer molecule and a reactive group $RG_2$ of the ROS scavenger molecules and is selected from the group consisting of:

| | $RG_1$ | $RG_2$ | Resulting Bond |
|---|---|---|---|
| a) | 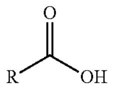 | $H_2N$—R | 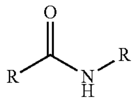 |
| | Acid | Primary Amine | Amide |

-continued

| | $RG_1$ | $RG_2$ | Resulting Bond |
|---|---|---|---|
| b) | 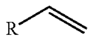 | 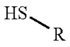 | 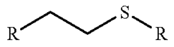 |
| | Double Carbon Bond | Thiol | Carbon-Thiol |
| c) | 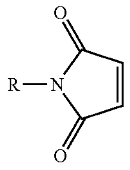 | 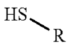 | 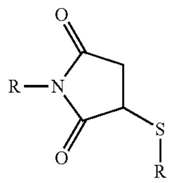 |
| | Maleimide | Thiol | Malamide-Thiol |
| d) | 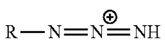 |  | 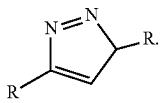 |
| | Azide | Alkyne | Triazole. |

16. The sensor of claim 1, wherein the ROS scavenger molecules reduce a degradation rate of the analyte indicator comprising the polymer.

17. The sensor of claim 1, wherein the sensor comprises at least one drug eluting polymer matrix that covers a portion of the sensor housing.

18. A method of fabricating a sensor for measurement of an analyte in a medium within a living animal, the method comprising:

applying an analyte indicator to a sensor housing of the sensor such that the applied analyte indicator covers at least a portion of the sensor housing, wherein the analyte indicator comprises a polymer; and coupling a plurality of reactive oxygen species (ROS) scavenger molecules covalently to the polymer, wherein the ROS scavenger molecules comprise

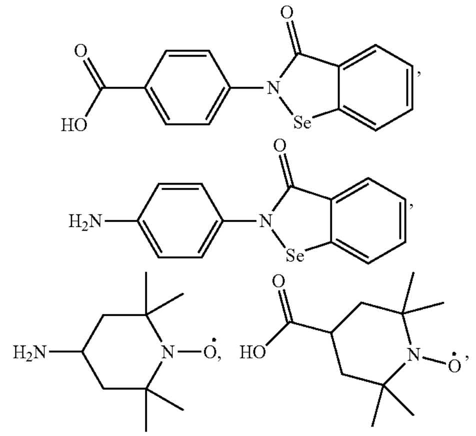

-continued

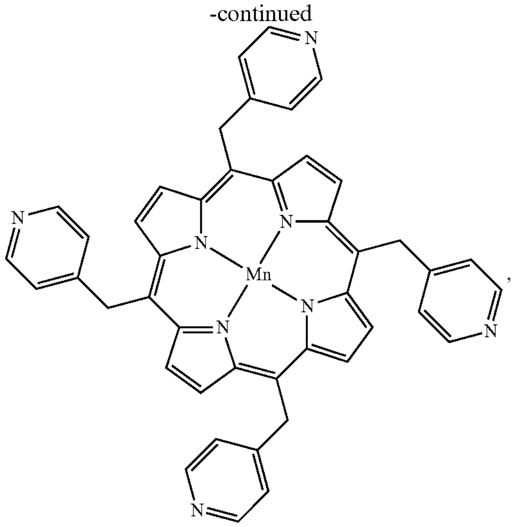

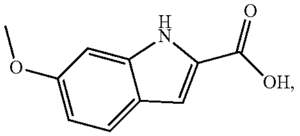

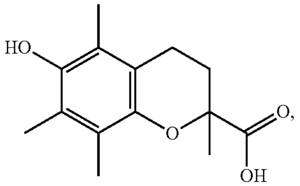

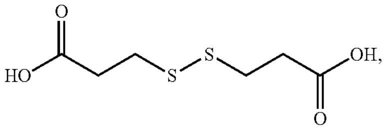

or a combination thereof.

19. The method of claim 18, wherein the polymer comprises co-monomers of at least monomers of A) an analyte indicator monomer, B) at least one acrylate, methacrylate, acrylamide, or methacrylamide monomer having a monomer spacer and a reactive group at an end thereof, and C) a polyethylene glycol monomer.

20. The method of claim 19, wherein coupling the plurality of ROS scavenger molecules covalently to the polymer comprises coupling the plurality of ROS scavenger molecules covalently to the reactive group of the analyte indicator such that each of the plurality of ROS scavenger molecules is covalently linked to the analyte indicator via the monomer spacer.

21. The method of claim 19, wherein A is 0.01 to 10% by weight, B is 1 to 99% by weight, and C is 1 to 99% by weight of the polymer.

22. The method of claim 19, wherein the polymer comprises co-monomers of four monomers according to Formula Ia: ABCD [Formula Ia], wherein A is the analyte indicator monomer, B is the at least one acrylate, methacrylate, acrylamide, or methacrylamide monomer having the monomer spacer and a reactive group at an end thereof, C is the polyethylene glycol monomer, and D is a compound or monomer containing boronate or boronic acid moieties, wherein A is 0.01 to 10% by weight, B is 1 to 99% by weight, C is 1 to 99% by weight, and D is 0.01 to 99% by weight of Formula Ia.

23. The method of claim 22, wherein the compound or monomer containing boronate or boronic acid moieties is selected from the group consisting of: a compound of formula II:

R—$B(OH)_2$ [Formula II], wherein R in Formula II is a hydrogen, hydroxyl, an alkyl group, an alkoxy group, an amino group, an aryl group, a heteroaryl, a cyclic group, a multicyclic group, or $NR_1R_2$, wherein $R_1$ and $R_2$ are identical or different and each represents a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, wherein Formula II optionally comprises a spacer or linker between R and B, a phenylboronic acid compound

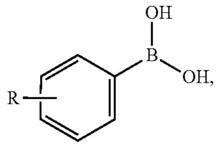

wherein one or more R in the phenylboronic acid compound is independently a hydrogen, hydroxyl, an alkyl group, an alkoxy group, an amino group, an aryl group, a heteroaryl, a cyclic group, a multicyclic group, or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, optionally comprising a spacer or linker between R and B, a boronate compound of Formula III:

[Formula III]

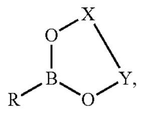

wherein R in Formula III is a hydrogen, hydroxyl, an alkyl group, an alkoxy group, an amino group, an aryl group, a heteroaryl, a cyclic group, a multicyclic group, or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and wherein X and Y=alkyl, wherein Formula III optionally comprises spacer or linker between R and B, and a combination thereof.

24. The method of claim 23, wherein the spacer or linker between R and B is a $C_1$-$C_{20}$ linear or branched alkyl or alkoxy.

25. The method of claim 23, wherein the compound containing boronate or boronic acid moieties is selected from the group consisting of: 2-acrylamidophenylboronic acid, 3-(Acrylamido)phenylboronic acid, 4-vinylboronic acid containing moieties, (3-methacrylamidophenyl)boronic acid, and a combination thereof.

26. The method of claim 23, wherein the compound containing boronate or boronic acid moieties is provided at a molar ratio of 0.1 to 100 to analyte indicator monomer.

27. The method of claim 20, wherein the polymer has a backbone, and the monomer spacer is covalently linked to the backbone of the polymer.

28. The method of claim 27, wherein the monomer spacer covalently linked to the backbone of the polymer comprises a poly(ethylene), poly(ethylene glycol), poly(vinyl alcohol), poly(pyrrolidone), poly(acrylamide), poly(acrylic acid), or poly(amine) group.

29. The method of claim 28, wherein the poly(ethylene), poly(ethylene glycol), poly(vinyl alcohol), poly(pyrrolidone), poly(acrylamide), poly(acrylic acid), or poly(amine) group is covalently linked to an acrylate, methacrylate, acrylamide, or methacrylamide group of the analyte indicator.

30. The method of claim 27, wherein the monomer spacer covalently linked to the backbone of the polymer comprises a flexible spacer having a repeating group selected from the group consisting of:

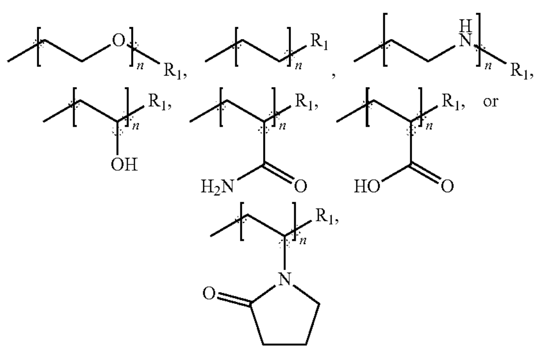

and a combination thereof, wherein $R_1$ is a reactive group and wherein n is 1 to 1000.

31. The method of claim 30, wherein the reactive group is

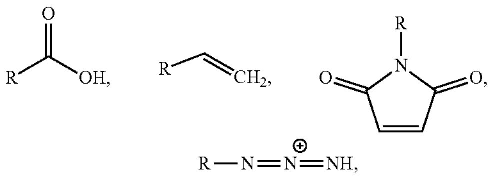

or

R—N=$\overset{\oplus}{N}$=NH, wherein R is the repeating group.

32. The method of claim 18, wherein the ROS scavenger molecules further comprise a reactive group attached thereto, wherein the reactive group is a primary amine, a thiol, or an alkyne group.

33. The method of claim 20, wherein the plurality of ROS scavenger molecules are covalently linked to the monomer spacer molecule via a coupling bond, wherein the coupling bond is an amide bond, a carbon-thiol bond, a malamide-thiol bond, or a triazole bond.

34. The method of claim 33, wherein the coupling bond is formed between a reactive group $RG_1$ of the monomer spacer molecule and a reactive group $RG_2$ of the ROS scavenger molecules selected from the group consisting of:

| | $RG_1$ | $RG_2$ | Resulting Bond |
|---|---|---|---|
| a) | 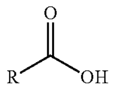 | $H_2N$—R | 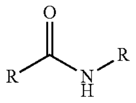 |
| | Acid | Primary Amine | Amide |
| b) | 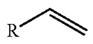 | 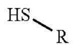 | 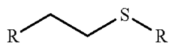 |
| | Double Carbon Bond | Thiol | Carbon-Thiol |
| c) | 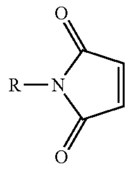 | 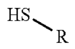 | 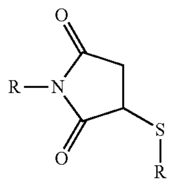 |
| | Maleimide | Thiol | Malamide-Thiol |
| d) | R—N=$\overset{\oplus}{N}$=NH | ≡—R | 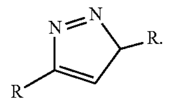 |
| | Azide | Alkyne | Triazole. |

35. The sensor of claim 1, wherein the ROS scavenger molecules comprises

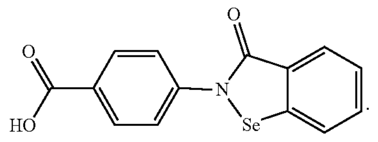 [SMILES: O=C(O)c1ccc(-n2[se]c3ccccc3c2=O)cc1]

36. The sensor of claim 1, wherein the ROS scavenger molecules comprises

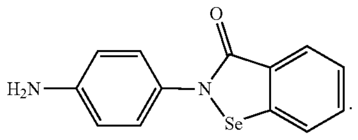 [SMILES: Nc1ccc(-n2[se]c3ccccc3c2=O)cc1]

37. The sensor of claim 1, wherein the ROS scavenger molecules comprises

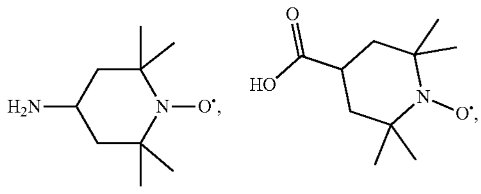

38. The sensor of claim 1, wherein the ROS scavenger molecules comprises,

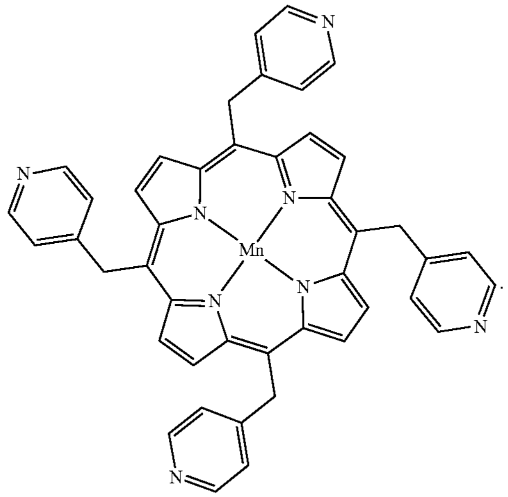

39. The sensor of claim 1, wherein the ROS scavenger molecules comprises

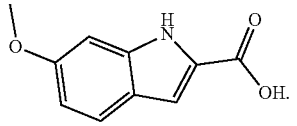

40. The sensor of claim 1, wherein the ROS scavenger molecules comprises

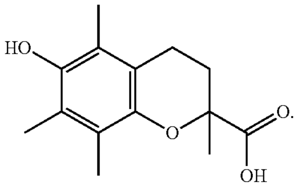 [SMILES: Cc1c(C)c2c(c(C)c1O)CCC(C)(C(=O)O)O2]

41. The sensor of claim 1, wherein the ROS scavenger molecules comprises

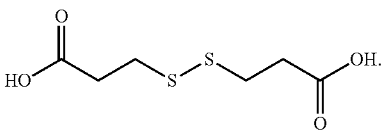 [SMILES: O=C(O)CCSSCCC(=O)O]

42. The method of claim 18, wherein the ROS scavenger molecules comprises

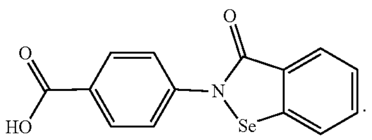 [SMILES: O=C(O)c1ccc(-n2[se]c3ccccc3c2=O)cc1]

43. The method of claim 18, wherein the ROS scavenger molecules comprises

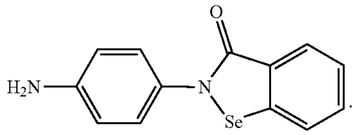 [SMILES: Nc1ccc(-n2[se]c3ccccc3c2=O)cc1]

44. The method of claim 18, wherein the ROS scavenger molecules comprises

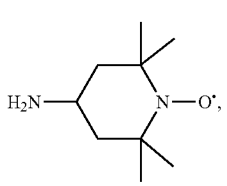
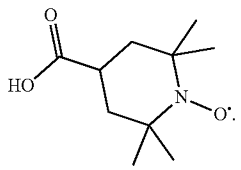

45. The method of claim 18, wherein the ROS scavenger molecules comprises,

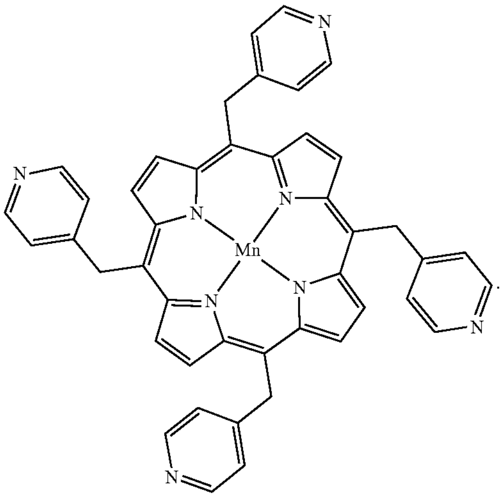

46. The method of claim 18, wherein the ROS scavenger molecules comprises

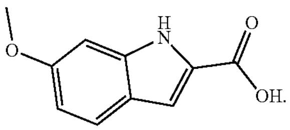

47. The method of claim 18, wherein the ROS scavenger molecules comprises

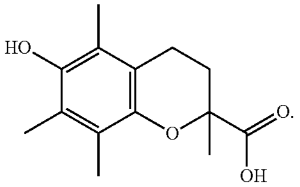 [SMILES: Cc1c(C)c2c(c(C)c1O)CCC(C)(C(=O)O)O2]

48. The method of claim 18, wherein the ROS scavenger molecules comprises

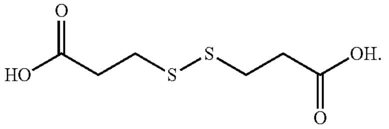 [SMILES: O=C(O)CCSSCCC(=O)O]

49. A sensor for measurement of an analyte in a medium within a living animal comprising:

a sensor housing;

an analyte indicator covering at least a portion of the sensor housing, wherein the analyte indicator comprises a polymer; and a plurality of reactive oxygen species (ROS) scavenger molecules covalently linked to the polymer via a monomer spacer molecule attached to the polymer, wherein the plurality of ROS scavenger molecules are covalently linked to the monomer spacer molecule via a coupling bond, wherein the coupling bond is an amide bond, a carbon-thiol bond, a malamide-thiol bond, or a triazole bond.

50. The sensor of claim 49, wherein the polymer has a backbone, and the monomer spacer is covalently linked to the backbone of the polymer.

51. The sensor of claim 50, wherein the polymer comprises co-monomers of at least monomers according to Formula Ia: ABC [Formula Ia], wherein A is an analyte indicator monomer, B is a acrylate, methacrylate, acrylamide, or methacrylamide monomer, C is a polyethylene glycol monomer, wherein A is 0.01 to 10% by weight, B is 1 to 99% by weight, and C is 1 to 99% by weight of Formula Ia.

52. The sensor of claim 50, wherein the polymer comprises co-monomers of four monomers according to Formula Ia: ABCD [Formula Ia], wherein A is an analyte indicator monomer, B is a acrylate, methacrylate, acrylamide, or methacrylamide monomer, C is a polyethylene glycol monomer, D is a compound or a monomer containing boronate or boronic acid moieties, wherein A is 0.01 to 10% by weight, B is 1 to 99% by weight, C is 1 to 99% by weight, and D is 0.01 to 99% by weight of Formula Ia.

53. The sensor of claim 52, wherein the compound or the monomer containing boronate or boronic acid moieties is selected from the group consisting of: a compound of formula II:

R—B$(OH)_2$ [Formula II], wherein R in Formula II is a hydrogen, hydroxyl, an alkyl group, an alkoxy group, an amino group, an aryl group, a heteroaryl, a cyclic group, a multicyclic group, or $NR_1R_2$, wherein $R_1$ and $R_2$ are identical or different and each represents a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, wherein Formula II optionally comprises a spacer or linker between R and B, a phenylboronic acid compound

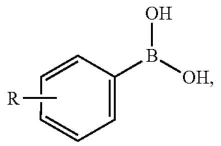

wherein one or more R in the phenylboronic acid compound is independently a hydrogen, hydroxyl, an alkyl group, an alkoxy group, an amino group, an aryl group, a heteroaryl, a cyclic group, a multicyclic group, or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, optionally comprising a spacer or linker between R and B, a boronate compound of Formula III:

[Formula III]

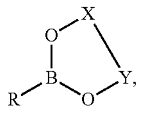

wherein R in Formula III is a hydrogen, hydroxyl, an alkyl group, an alkoxy group, an amino group, an aryl group, a heteroaryl, a cyclic group, a multicyclic group, or $NR_1R_2$ wherein $R_1$ and $R_2$, identical or different, each represent a hydrogen atom, a hydroxyl group, an alkyl group, an alkoxy group, an amino group, an aryl group, a heteroaryl, a cyclic group, a multicyclic group, a carboxylic acid, a vinyl group, an acrylate group, an acryloyl group, or a methacrylate group, and wherein X and Y=alkyl, wherein Formula III optionally comprises a spacer or linker between R and B, and a combination thereof.

54. The sensor of claim 53, wherein the spacer or linker between R and B is a $C_1$-$C_{20}$ linear or branched alkyl or alkoxy.

55. The sensor of claim 52, wherein the compound containing boronate or boronic acid moieties is selected from the group consisting of: 2-acrylamidophenylboronic acid, 3-(Acrylamido)phenylboronic acid, 4-vinylboronic acid containing moieties, (3-methacrylamidophenyl)boronic acid, and a combination thereof.

56. The sensor of claim 50, wherein the monomer spacer covalently linked to the backbone of the polymer comprises a poly(ethylene), poly(ethylene glycol), poly(vinyl alcohol), poly(pyrrolidone), poly(acrylamide), poly(acrylic acid), or poly(amine) group.

57. The sensor of claim 56, wherein the poly(ethylene), poly(ethylene glycol), poly(vinyl alcohol), poly(pyrrolidone), poly(acrylamide), poly(acrylic acid), or poly(amine)

group is covalently linked to an acrylate, methacrylate, acrylamide, or methacrylamide group of the polymer.

58. The sensor of claim 50, wherein the monomer spacer covalently linked to the backbone of the polymer comprises a flexible spacer having a repeating group selected from the group consisting of:

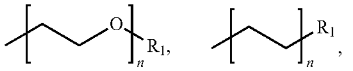

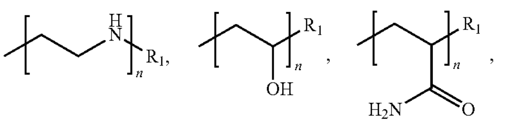

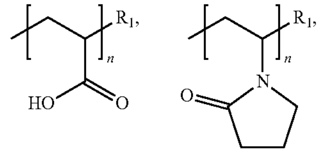

and a combination thereof, wherein $R_1$ is a reactive group and wherein n is 1 to 1000.

59. The sensor of claim 58, wherein the reactive group is

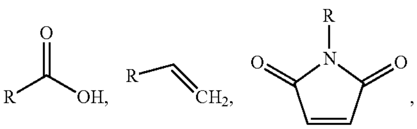

, or $R—N{=}\overset{\oplus}{N}{=}NH$, wherein R is the repeating group.

60. The sensor of claim 49, wherein the ROS scavenger molecules comprise

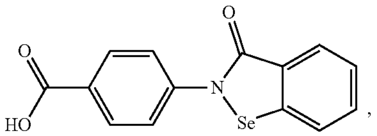

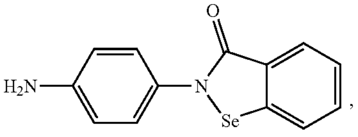

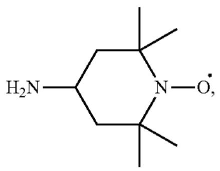

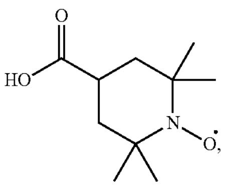

-continued

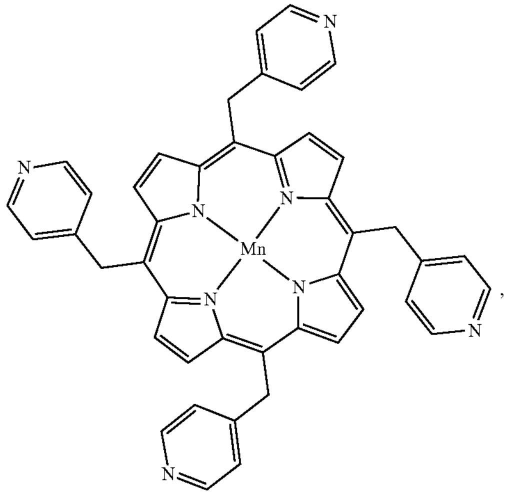

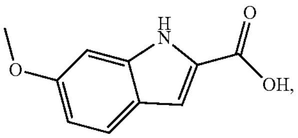

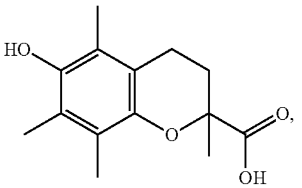

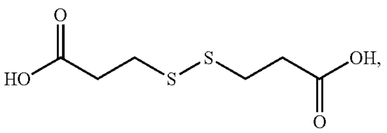

or a combination thereof.

61. The sensor of claim 60, wherein the ROS scavenger molecules further comprise a reactive group attached thereto, wherein the reactive group is a primary amine, a thiol, or an alkyne group.

62. The sensor of claim 49, wherein the coupling bond is formed between a reactive group $RG_1$ of the monomer spacer molecule and a reactive group $RG_2$ of the ROS scavenger molecules selected from the group consisting of:

| | $RG_1$ | $RG_2$ | Resulting Bond |
|---|---|---|---|
| a) | 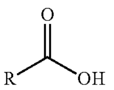 Acid | $H_2N—R$ Primary Amine | 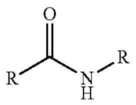 Amide |
| b) | 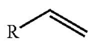 Double Carbon Bond | 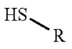 Thiol | 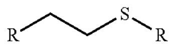 Carbon-Thiol |

-continued
| | $RG_1$ | $RG_2$ | Resulting Bond |
|---|---|---|---|
| c) | 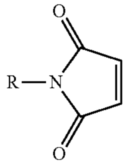 Maleimide | 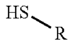 Thiol | 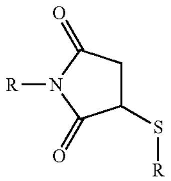 Malamide-Thiol |
| d) | 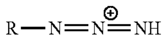 Azide | 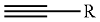 Alkyne | 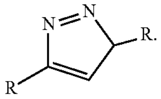 Triazole. |
63. The sensor of claim 49, wherein the sensor comprises at least one drug eluting polymer matrix that covers a portion of the sensor housing.
* * * * *